US010946104B2

(12) United States Patent
Renes et al.

(10) Patent No.: US 10,946,104 B2
(45) Date of Patent: Mar. 16, 2021

(54) ABERRANT CELL-RESTRICTED IMMUNOGLOBULINS PROVIDED WITH A TOXIC MOIETY

(71) Applicant: APO-T B.V., Amersfoort (NL)

(72) Inventors: Johan Renes, Amersfoort (NL); Paul Steverink, Amersfoort (NL); Ralph Alexander Willemsen, Rotterdam (NL)

(73) Assignee: APO-T B.V., Amersfoort (NL)

( * ) Notice: Subject to any disclaimer, the term of this patent is extended or adjusted under 35 U.S.C. 154(b) by 0 days.

(21) Appl. No.: 14/372,094

(22) PCT Filed: Jan. 11, 2013

(86) PCT No.: PCT/NL2013/050014
§ 371 (c)(1),
(2) Date: Jul. 14, 2014

(87) PCT Pub. No.: WO2013/105856
PCT Pub. Date: Jul. 18, 2013

(65) Prior Publication Data
US 2015/0056198 A1    Feb. 26, 2015

Related U.S. Application Data

(60) Provisional application No. 61/586,568, filed on Jan. 13, 2012.

(51) Int. Cl.
| A61K 47/68 | (2017.01) |
| C07K 16/28 | (2006.01) |
| C07K 16/30 | (2006.01) |
| C07K 16/08 | (2006.01) |
| C07K 16/32 | (2006.01) |
| C07K 16/40 | (2006.01) |
| A61P 35/00 | (2006.01) |
| A61K 39/00 | (2006.01) |

(52) U.S. Cl.
CPC ...... *A61K 47/6813* (2017.08); *A61K 47/6809* (2017.08); *A61K 47/6849* (2017.08); *A61K 47/6851* (2017.08); *A61K 47/6883* (2017.08); *A61P 35/00* (2018.01); *C07K 16/084* (2013.01); *C07K 16/085* (2013.01); *C07K 16/2833* (2013.01); *C07K 16/2884* (2013.01); *C07K 16/30* (2013.01); *C07K 16/3069* (2013.01); *C07K 16/3092* (2013.01); *C07K 16/32* (2013.01); *C07K 16/40* (2013.01); *A61K 2039/505* (2013.01); *C07K 2317/32* (2013.01); *C07K 2317/34* (2013.01); *C07K 2317/569* (2013.01); *C07K 2317/76* (2013.01); *C07K 2319/33* (2013.01)

(58) Field of Classification Search
None
See application file for complete search history.

(56) References Cited

U.S. PATENT DOCUMENTS

| 5,709,995 A | 1/1998 | Chisari et al. |
| 6,737,056 B1 | 5/2004 | Presta |
| 7,488,793 B2 | 2/2009 | Van et al. |
| 7,635,472 B2 | 12/2009 | Kufer et al. |
| 8,568,717 B2 | 10/2013 | De et al. |
| 9,260,508 B2 | 2/2016 | Laeremans et al. |
| 9,512,231 B2 | 12/2016 | Willemsen |
| 9,821,073 B2 | 11/2017 | Willemsen et al. |
| 2003/0223994 A1 | 12/2003 | Hoogenboom et al. |
| 2004/0162411 A1 | 8/2004 | Lanzavecchia |
| 2004/0219643 A1 | 11/2004 | Winter et al. |
| 2005/0026881 A1 | 2/2005 | Robinson et al. |
| 2005/0037421 A1 | 2/2005 | Honda et al. |
| 2005/0084449 A1 | 4/2005 | Landes et al. |
| 2005/0136050 A1 | 6/2005 | Kufer et al. |
| 2005/0175606 A1 | 8/2005 | Huang et al. |
| 2005/0255101 A1 | 11/2005 | Reiter et al. |
| 2005/0266425 A1 | 12/2005 | Zauderer et al. |
| 2005/0287141 A1 | 12/2005 | Reiter et al. |
| 2006/0135418 A1 | 6/2006 | Jakobsen et al. |
| 2006/0263381 A1 | 11/2006 | Kosmatopoulos et al. |
| 2007/0140966 A1 | 6/2007 | Chang et al. |
| 2008/0044413 A1 | 2/2008 | Hammond et al. |
| 2008/0280346 A1 | 11/2008 | De et al. |

(Continued)

FOREIGN PATENT DOCUMENTS

| GB | 0115841 | 2/1919 |
| GB | 0601513 | 5/1948 |

(Continued)

OTHER PUBLICATIONS

Ducry et al. ("Ducry", Bioconjugate Chem. 2010, 21, 5-13).*
Chames et al. ("Chames", J. Immunol. 2002, 169, 1110-1118, cited in IDS filed Jul. 14, 2014).*
Gatz et al. ("Gatz", Tissue Antigens, 2002, 55, 532-547).*
Graff-Dubois et al. ("Graff" J. Immunol, 2002, 169, 575-80).*
Rudikoff et al. (PNAS USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444.*

(Continued)

*Primary Examiner* — Karl J Puttlitz
*Assistant Examiner* — Kauser M Akhoon
(74) *Attorney, Agent, or Firm* — TraskBritt

(57) ABSTRACT

Described are immunoglobulins provided with a toxic moiety, comprising at least an immunoglobulin variable region that specifically binds to an MHC-peptide complex preferentially associated with aberrant cells. These immunoglobulins provided with a toxic moiety are preferably used in selectively modulating biological processes. The provided immunoglobulins provided with a toxic moiety are of particular use in pharmaceutical compositions for the treatment of diseases related to cellular aberrancies, such as cancers and autoimmune diseases.

11 Claims, 5 Drawing Sheets

Specification includes a Sequence Listing.

(56) References Cited

U.S. PATENT DOCUMENTS

| | | |
|---|---|---|
| 2009/0155275 A1 | 6/2009 | Wu et al. |
| 2009/0169548 A1 | 7/2009 | Grosveld et al. |
| 2009/0208502 A1 | 8/2009 | Willemsen |
| 2009/0268502 A1 | 10/2009 | Miura et al. |
| 2009/0269277 A1 | 10/2009 | Chang et al. |
| 2009/0304693 A1 | 12/2009 | Ghayur et al. |
| 2010/0029497 A1 | 2/2010 | Himmler et al. |
| 2010/0062001 A1 | 3/2010 | Reiter et al. |
| 2010/0158927 A1 | 6/2010 | Reiter et al. |
| 2010/0228007 A1 | 9/2010 | Hoogenboom et al. |
| 2010/0322935 A1 | 12/2010 | Croasdale et al. |
| 2011/0059076 A1 | 3/2011 | McDonagh et al. |
| 2011/0091446 A1 | 4/2011 | De et al. |
| 2011/0110851 A1 | 5/2011 | Chang et al. |
| 2011/0318369 A1 | 12/2011 | Reiter et al. |
| 2012/0244578 A1 | 9/2012 | Kannan et al. |
| 2013/0011375 A1 | 1/2013 | Chen |
| 2013/0183307 A1 | 7/2013 | Renes et al. |
| 2013/0202527 A1 | 8/2013 | Tse et al. |
| 2014/0120090 A1 | 5/2014 | Willemsen |
| 2014/0205599 A1 | 7/2014 | Willemsen |
| 2014/0227273 A1 | 8/2014 | Willemsen et al. |
| 2014/0336475 A1 | 11/2014 | Renes |
| 2015/0056198 A1 | 2/2015 | Renes et al. |
| 2015/0175683 A1 | 6/2015 | Renes et al. |
| 2015/0202318 A1 | 7/2015 | Renes et al. |
| 2017/0114144 A1 | 4/2017 | Willemsen |
| 2018/0071398 A1 | 3/2018 | Willemsen et al. |
| 2018/0105587 A1 | 4/2018 | Renes et al. |

FOREIGN PATENT DOCUMENTS

| | | |
|---|---|---|
| GB | 1380341 A | 1/1975 |
| JP | 2003-525016 A | 8/2003 |
| JP | 2005-501517 A | 1/2005 |
| JP | 2005-504524 A | 2/2005 |
| JP | 2005-521389 A | 7/2005 |
| JP | 2005-533486 A | 11/2005 |
| JP | 2006-523437 A | 10/2006 |
| JP | 2008-501781 A | 1/2008 |
| JP | 2008-523783 A | 7/2008 |
| JP | 2009-515897 A | 4/2009 |
| JP | 2009-524422 A | 7/2009 |
| JP | 2009-541361 | 11/2009 |
| JP | 2010-154864 A | 7/2010 |
| JP | 2010-535032 A | 11/2010 |
| JP | 2011-063603 A | 3/2011 |
| JP | 2011-097943 A | 5/2011 |
| JP | 2012-528092 A | 11/2012 |
| JP | 2014-505471 A | 3/2014 |
| WO | 9201699 A1 | 2/1992 |
| WO | 9635696 A1 | 11/1996 |
| WO | 9845304 A1 | 10/1998 |
| WO | 99/08108 A1 | 2/1999 |
| WO | 99/42077 A2 | 8/1999 |
| WO | 00/23087 A1 | 4/2000 |
| WO | 00/31239 A1 | 6/2000 |
| WO | 02/79222 A2 | 10/2002 |
| WO | 02/83738 A1 | 10/2002 |
| WO | 03040722 A1 | 5/2003 |
| WO | 03068201 A2 | 8/2003 |
| WO | 03/83124 | 10/2003 |
| WO | 03/89467 A1 | 10/2003 |
| WO | 2004/003019 A2 | 1/2004 |
| WO | 2004/050705 A2 | 6/2004 |
| WO | 2004/106380 A2 | 12/2004 |
| WO | 2005/113595 | 12/2005 |
| WO | 2005120166 A2 | 12/2005 |
| WO | 2006/037960 A2 | 4/2006 |
| WO | 2007/059082 A1 | 5/2007 |
| WO | 2007/073147 A1 | 6/2007 |
| WO | 2007/085837 A1 | 8/2007 |
| WO | 2008/120202 A2 | 10/2008 |
| WO | 2009/018386 A1 | 2/2009 |
| WO | 2009/058383 A2 | 5/2009 |
| WO | 2009131435 A1 | 10/2009 |
| WO | 2009/149185 A2 | 12/2009 |
| WO | 2010/037838 A2 | 4/2010 |
| WO | 2010/133828 A1 | 11/2010 |
| WO | 2010/136172 A1 | 12/2010 |
| WO | 2011/001152 A1 | 1/2011 |
| WO | 2011/063348 A1 | 5/2011 |
| WO | 2011/064664 A2 | 6/2011 |
| WO | 2011/085473 A1 | 7/2011 |
| WO | 2012091563 A1 | 7/2012 |
| WO | 2012091564 A2 | 7/2012 |
| WO | 2013/048243 A1 | 4/2013 |
| WO | 2013105856 A1 | 7/2013 |
| WO | 2014/003552 A1 | 1/2014 |

OTHER PUBLICATIONS

Gussow et al. (1991, Methods in Enzymology 203:99-121).*

Ibragimova and Wade (Biophysical Journal, , 1999, 77, 2191-2198.*

Tatiana et al., Antibody Specific for the PeptideMajor Histocompatibility Complex: Is it T cell receptor-like? Journal of Biological Chemistry, Oct. 22, 2004, pp. 44243-44249, vol. 279, No. 43, American Society for Biochemistry and Molecular Biology, US.

Cohen et al., Direct detection and quantitation of a distinct T-cell epitope derived from tumor-specific epithelial cell-associated mucin using human recombinant antibodies endowed with the antigen-specific, . . . complex-restricted specificity of T-cells, Cancer Research, Oct. 15, 2002, pp. 5835-5844, vol. 62, American Association for Cancer Research, US.

Chames et al., TCR-like human antibodies expressed on human CTLs mediate antibody affinity-dependent cytolytic activity, The Journal of Immunology, Jul. 15, 2002, pp. 1110-1118, vol. 169, No. 2, The American Association of Immunologists, US.

Avital et al., Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit, Cancer Research, Jun. 1, 2002, pp. 3184-3194, vol. 62, American Association for Cancer Research.

Yael et al., Expression Hierarchy of T Cell Epitopes from Melanoma Differentiation Antigens: Unexpected High Level Presentation of Tyrosinase-HLA-A2 Complexes Revealed by Peptide-Specific, MHC-Restricted, TCR-Like Antibodies, The Journal of Immunology, May 15, 2009, pp. 6328-6341, vol. 182, No. 10, The American Association of Immunologists, US.

Stish et al., Increasing Anticarcinoma Activity of an Anti-erbB2 Recombinant Immunotoxin by the Addition of an Anti-EpCAM sFv, Clinical Cancer Research, May 15, 2007, pp. 3058-3067, vol. 13, No. 10.

Dorvillius et al., Targeting of Human Breast Cancer by a Bispecific Antibody Directed Against Two Tumour-Associated Antigens: ERBB-2 and carcinoembryonic Antigen, Tumor Biology, Jan. 1, 2002, pp. 337-347, vol. 23, Karger, Basel, CH.

PCT International Search Report, PCT/NL20013/050014, dated Jun. 4, 2013.

Chinnasamy et al., J. Immunol. 2011, 1886:685-96 (pub-d online Dec. 13, 2010).

Chames et al., Direct selection of a human antibody fragment directed against the tumor T-cell epitope HLA-A1-MAGE-A1 from a nonimmunized phage-Fab library, PNAS, Jul. 5, 2000 , vol. 97 No. 14 pp. 7969-7974.

Chomez et al., An Overview of the MAGE Gene Family with the Identification of All Human Members of the Family, Jul. 15, 2001, Cancer Research 61, pp. 5544-5551.

Denkberg et al., Selective Targeting of Melanoma and APCs Using a Recombinant Antibody with TCR-Like Specificity Directed Toward a Melanoma Differentiation Antigen, The Journal of Immunology, 2003, 171: pp. 2197-2207.

Harmsen et al., Properties, production, and applications of camelid single-domain antibody fragments, Appl Microbiol Biotechnol, (2007), 77: pp. 13-22.

(56) References Cited

OTHER PUBLICATIONS

Casset et al., A peptide mimetic of an anti-CD4 monoclonal antibody by rational design, BBRC, 2003, pp. 198-205, vol. 307, Elsevier.
Burks et al. (PNAS 94:412-417 (1997)).
Brummell et al. (Biochemistry 32:1180-1187 (1993)).
Brorson et al., J. Immunol., 1999, vol. 163, pp. 6694-6701.
Zarour et al (Cancer Res., 2000, 60: 4946-4952).
Ying et al., The Journal of Biological Chemistry, Jun. 1, 2012, vol. 287, pp. 19399-19408.
Wu et al. (J. Mol. Biol. (1999) 294, 151-162).
Willemsen et al: "A phage display selected Fab fragment with MHC class I-restricted specificity for MAGE-A1 allows for retargeting of primary human T lymphocytes", Gene Therapy, vol. 8, No. 21, Nov. 1, 2001 (Nov. 1, 2001), pp. 1601-1608, XP55028813, ISSN: 0969-7128, DOI: 10.1038/sj.gt.3301570 the whole document.
Willemsen et al., Cytometry, 2008, vol. 73A, pp. 1093-1099.
Ward et al. (Nature 341:544-546 (1989)).
Wang, X. et. al., A new Recombinant Single Chain Trispecific Antibody Recruits T lymphocytes to Kill CEA (Carcinoma Embryonic Antigen) Positive Tumor Cells In Vitro Efficiently, Journal of Biochemistry, 2004, 135 (4) 555-565.
Vincke & Muyldermans, Chapter 2 in: Single Domain Antibodies: Methods and Protocols, D. Saerens & S. Muyldermans, eds, Methods Mol. Biol. 911:15-26 (2012).
Vajdos et al. ((2002) J. Mol. Biol. 320, 415-428).
Stork, R. el. al., A novel tri-functional antibody fusion protein with improved pharmacolonetic properties generated by fusing a bispecific single-chain diabody. with an albumin-binding domain from streptococcal protein G, Protein Engineering, Design & Selection,2007, 20 (11), 569-576.
Stancovski et al., Proceedings of the National Academy of Science USA 88: 8691-8695, 1991.
Song et al. (Biochem Biophys Res Comm 268:390-394 (2000)).
Smith-Gill et al. (J. Immunol. 139:4135-4144 (1987)).
Sekimoto et al. (Cancer Res 2007; 67: (3): 1184-1192; Feb. 1, 2007).
Segal, DM. et al., and Introduction: bispecific antibodies, Journal of Immunological Methods, and 2001,248,1-6.
Schoonjans R. et. al., Fab Chains as an Efficient Heterodimerization Scaffold for the Production of Recombinant Bispecific and TrispecificAntibody Derivatives, The Journal of Immunology, 2000, 165, 7050-7057.
Schmidt M. el. al., Targeted inhibition of tumor cell growth by a bispecific single chain toxin containing an antibody domain and TGFalpha, British Journal of Cancer, 1996, 74,853-862.
Saerens D et al: "Single-domain antibodies as building blocks for novel therapeutics", Current Opinion in Pharmacology, Elsevier vol. 8, No. 5, Oct. 1, 2008 (Oct. 1, 2008), pp. 600-608, XP025609339, ISSN: 1471-4892, DOI: 10.1016/J.COPH.2008.07.006 retrieved on Aug. 22, 2008.
PCT Written Opinion PCT/NL2013/050453, dated Oct. 21, 2013.
PCT International Preliminary Report on Patentability, PCT/NL2013/050453, dated Dec. 31, 2014.
Paul, Fundamental Immunology, 3rd Edition, 1993, pp. 292-295.
Pathogen-associate molecular pattern, Wikipedia, available at : https://en.wikipedia.org/wiki/Pathogen-associated_molecular_pattern, visited May 25, 2017.
Ozaki S. ((2011) Diabody. In: Schwab M. (eds) Encyclopedia of Cancer. Springer, Berlin, Heidelberg; definition of "diabody"; link. springer.com/referenceworkentry/10.1007%2F978-3-642-16483-5_1603).
Newton et al., Signaling in Innate Immunity and Inflammation, 2012, pp. 1-19, Cold Spring Harbor.
Muyldermans et al., Reviews in Molecular Biotechnology 74: 277-302 (Year: 2001).
Muraoka et al (J. Biochem. 2009; 145(6)799-810).
Monegal et al., Protein Design & Selection, 2009; 22(4):273-280.
MacCallum et al., J. Mole Biol. 1996, vol. 262, pp. 732-745.

Liu, J. el. al., A new format of single chain tri-specific antibody with diminished molecular size sufficiently infuses ovarian tumor cell killing, Biotechnology Letters, 2005, 27, 1821-1827.
Kurogiet al., An antibody therapy of cancer besides, Biotherapy, 2005, 19 (2), 125-132.
Kumar et al. (J. Biol. Chem. 275:35129-35136 (2000)).
Kobayashi et al. (Protein Engineering 12:879-844 (1999)).
Kawakami, Yutaka, Identification of Human Melanoma Antigens Recognized by T Cells and Their Use for Immune-Gene Therapy, http://www.jstage.jst.go.jp/article/jslrt1997/37/3/37_3_137_article/-ch . . . Visited Sep. 28, 2018.
Jung, G. et al., and Target. cell induced T cell activation with bi- and trispecific antibody fragments, European Journal of Immunology, 1991,21,2431.
Jongmans, W. et al., Targeting of Adenovirus to human renal cell carcinoma cells, Urology, 2003, 62,559-565.
Japanese Notification for Reason of Refusal dated Jun. 24, 2016, 4 pages.
Jang et al., Mclec. Immunol., 1998, vol. 35, pp. 1207-1217.
Jager et al. (PNAS, 2000, 97(22): 12198-12203).
International Search Report for Patent Cooperation Treaty Application No. PCT/NL2012/050675, dated Jan. 2, 2013, 5 pages.
International Search Report and Written Opinion received for PCT Patent Application No. PCT/NL2011/050893, dated Jun. 6, 2012, 9 pages.
International Search Report and Written Opinion received for PCT Patent Application No. PCT/NL11/50891, dated Jun. 12, 2012, 11 pages.
International Preliminary Report on Patentability received for PCT Patent Application No. PCT/NL2012/050675, dated Apr. 10, 2014, 6 pages.
International Preliminary Report on Patentability received for PCT Patent Application No. PCT/NL2011/050893, dated Jul. 11, 2013, 7 pages.
International Preliminary Report on Patentability received for PCT Patent Application No. PCT/NL11/50891, dated Jul. 11, 2013, 8 pages.
Hudson, P. et al., High acidity scFv multimers; diabodies and triabodies, Journal of Immunological Methods, 1999, 231,177-189.
Holm et al., 2007, Mol. Immunol., vol. 44, pp. 1075-1084.
Hickman, Cancer and Metastasis Reviews 11:121 1992.
De Pascalis et al., Grafting of "Abbreviated" Complementarity-Determining Regions Containing Specificity-Determining Residues Essential for Ligand Contact to Engineer a Less Immunogenic Humanized Monoclonal Antibody, The Journal of Immunology, 2002, pp. 3076-3084, vol. 169.
Davies et al., Protein Engineering 9(6): 531-537, 1996.
Chen et al. J. Mol. Bio. (1999) 293, 865-881.
Japanese Written Opinion for Japanese Application No. 2014-552149, dated Feb. 28, 2017, 30 pages with English Translation.
Sadofsky "The RAG proteins in V{D)J recombination: more than just a nuclease" Nucleic Acids Research, 2001, vol. 29, No. 7 1399-1409.
Chinnasamy N et al and a TCR targeting the HLA-A*0201-restricted epitope of MAGE-A3 recognizes multiple epitopes of the MAGE-A antigen superfamily in several types of cancer, J Immunology, 2011, vol. 186,685-696.
Ducry L & Stump B, Antibody-drug conjugates: linking cytotoxic payloads to monoclonal antibodies and Bioconjug Chem, 2010, and vol. 21 No. 1, 5-13.
Dunbar et al. Examining Variable Domain Orientations in Antigen Receptors Gives Insight into TCR-Like Antibody Design LOA computational Biology, www.ploscompbiol.org, Article dated Sep. 2014; vol. 10 Issue 9, (10 pages).
Edwards et al., J Mol Biol 334(1): 103-118 (Year: 2003).
European Search Report and Search Opinion Received for EP Application No. 18207894, dated Feb. 4, 2019, 10 pages.
Graff-Dubois S et al: "Generation of CTL Recognizing an HLA-A 0201-Restricted Epitope Shared by MAGE-A1, -A2, -A3, -A4,-A6, -A10, and -A12 Tumor Antigens: Implication in a Broad-Spectrum Tumor Immunotherapy", The Journal of Immunology, The American Association of Immunologists, US, vol. 169, No. 1, Jan. 1, 2002 (Jan. 1, 2002), pp. 575-580.

(56) References Cited

OTHER PUBLICATIONS

Holliger et al., "Engineered antibody fragments and the rise of single domains", Nat Biotechnol., vol. 23, No. 9, (Sep. 2005), pp. 1126-1136.
Houghton et al., N.E., Immunity against cancer: lessons learned from melanoma. Curr Opin Immunol 2001, 13, 134-40.
International Written Opinion for International Application No. PCT/NL2013/050014, dated Jun. 4, 2013, 5 pages.
Isolation and identification of human melanoma antigens recognized by Kawakami, T cells, application for immunogene therapy, Journal of the Japan Lymphoreticular System, 1997, vol. 37, No. 3, pp. 137-144.
Japanese Decision of Refusal for Japanese Application No. 2014-552149, dated Aug. 1, 2017, 9 pages with English Translation.
Japanese Notice of Reasons for Refusal for Japanese Application No. 2014-552149, dated Nov. 29, 2016, 10 pages with English Translation.
Japanese Notice of Reasons for Refusal for Japanese Application No. 2017-232042, dated Nov. 29, 2018, 8 pages with English Translation.
Japanese Search Report for Japanese Application No. 2014-552149, dated Nov. 17, 2016, 37 pages with English Translation.
Klechevsky E et al and Antitumor activity of immunotoxinswith Tcell receptor-like apecificity against human melanoma xenografts, Cancer Res, 2008, vol. 68 No. 15-6360-6367.
Li et al. "Construction and characterization of a humanized anti-human CD3 monoclonal antibody 12F6 with effective immunoregulation functions" Article (2005) pp. 487-498.
Lloyd et al., Protein Engineering, Design & Selection 22: 159-168 (Year: 2009).
Masaaki Satoh et al: "Monoclonal Antibody 2-152a Suppresses Hepatitis C Virus Infection Through Betaine/GABA Transporter-1", Journal of Nfectious Diseases. JID, vol. 204, No. 8, Oct. 15, 2011 (Oct. 15, 2011), pp. 1172-1180.
Michaeli et al., Expression Hierarchy of T Cell Epitopes from Melanoma Differentiation Antigens: Unexpected High Level Presentation of Tyrosinase-HLA-A2 Complexes Revealed by Peptide-Specific, MHC-Restricted, TCR-Like Antibodies, The Journal of Immunology, May 15, 2009, pp. 6328-6341, vol. 182, No. 10, The American Association of Immunologists, US.
Nguyen et al., EMBO J 19(5): 921-930 (Year: 2000).
Parmiani et al. "Unique human tumor antigens: immunobiology and use in clinical trials", J Immunol 2007, 178, 1975-9.
Reynolds Gary M et al: "Hepatitis C virus receptor expression in normal and diseased liver tissue", Hepatology, John Wiley & Sons, Inc, US, vol. 47, No. 2, Feb. 1, 2008 (Feb. 1, 2008), pp. 418-427, XP002516760, ISSN: 0270-9139, DOI: 10.1002/HEP.22028.
Ridgway et al. "Knobs-into-holes" engineering of antibody CH3 domains for heavy chain heterodimerization, Protein Engineering 1996, 9(7), 617-621.
The Journal of Immunology, 2011, and vol. 186 and pp. 685-696.
Van Den Eynde et al. "T cell-defined tumor antigens" Curr Opin Immunol 1997, 9, 684-93.
Van Der Bruggen et al. , "Tumor-specific shared antigenic peptides recognized in human T cells", Immunol Rev 2002, 188, 51-64.
Bent Jakobsen: "Immunocore powerpoint presentation", iSBTc Washington, Oct. 30, 2009 (Oct. 30, 2009), pp. 1-19, XP055485474, Retrieved from the Internet: URL:https://sitc.sitcancer.org/meetings/am09/presentations/fri/Jakobsen.pdf [retrieved on Jun. 19, 2018].
Claude Backendorf et al: "Apoptin: Therapeutic Potential of an Early Sensor of Carcinogenic Transformation", Annual Review of Pharmacology and Toxicology, vol. 48, No. 1, Feb. 1, 2008 (Feb. 1, 2008), pp. 143-169, XP055139454, ISSN: 0362-1642, DOI: 10.1146/annurev.pharmtox.48.121806.154910.
European Communication pursuant to Article 94(3) EPC for European Application No. 11820898, dated Jun. 20, 2016, 7 pages.
European Communication pursuant to Article 94(3) EPC for European Application No. 11820898, dated Sep. 11, 2018, 5 pages.
European Communication pursuant to Article 94(3) EPC for European Application No. 11820898, dated Sep. 16, 2014, 6 pages.
European Communication pursuant to Article 94(3) EPC for European Application No. 11820898, dated Sep. 21, 2017, 6 pages.
European Communication pursuant to Article 94(3) EPC for European Application No. 11820899, dated Aug. 4, 2016, 4 pages.
European Communication pursuant to Article 94(3) EPC for European Application No. 11820899, dated Mar. 20, 2018, 3 pages.
European Communication pursuant to Article 94(3) EPC for European Application No. 11820899, dated Nov. 17, 2015, 3 pages.
European Communication pursuant to Article 94(3) EPC for European Application No. 12772530, dated Jan. 27, 2016, 3 pages.
European Communication pursuant to Article 94(3) EPC for European Application No. 13703480, dated Aug. 24, 2015, 4 pages.
European Communication pursuant to Article 94(3) EPC for European Application No. 13703480, dated Oct. 7, 2016, 5 pages.
European Communication pursuant to Article 94(3) EPC for European Application No. 13703480, dated Sep. 20, 2017, 5 pages.
European Communication pursuant to Article 94(3) EPC for European Application No. 13737682, dated Feb. 17, 2017, 5 pages.
European Communication pursuant to Article 94(3) EPC for European Application No. 13737682, dated May 2, 2016, 5 pages.
European Search and Opinion for European Application No. 18153459, dated Jun. 28, 2018, 9 pages.
H-Y Zhang et al: "Tumor-targeted delivery of biologically active TRAIL protein", Cancer Gene Therapy, Appleton & Lange, GB, vol. 17, May 1, 2010 (May 1, 2010), pp. 334-343, XP002660326, ISSN: 0929-1903, DOI: 10.1038/CGT2009.76 [retrieved on Jan. 15, 2010].
K. Breckpot et al: "Identification of New Antigenic Peptide Presented by HLA-Cw7 and Encoded by Several MAGE Genes Using Dendritic Cells Transduced with Lentiviruses", The Journal of Immunology, vol. 172, No. 4, Feb. 5, 2004 (Feb. 5, 2004), pp. 2232-2237, XP055485920, us ISSN: 0022-1767, DOI: 10.4049/jimmunol.172.4.2232.
Nathaniel Liddy et al: "Monoclonal TCR-redirected tumor cell killing", Nature Medicine, vol. 18, No. 6, May 6, 2012 (May 6, 2012), pp. 980-987, XP055241791 New York ISSN: 1078-8956, DOI: 10.1038/nm.2764.
Noy R et al: "T-Cell Receptor-Like Antibodies: Novel Reagents for Clinical Cancer Immunology and Immunotherapy", Expert Review of Anticancer the, Expert Reviews Ltd, GB, vol. 5, No. 3, Jun. 1, 2005 (Jun. 1, 2005), pp. 523-536, XP009067037, ISSN: 1473-7140, DOI: 10.1586/14737140.5.3.523.
P Bruno et al: "Family at last: highlights of the first international meeting on proteins killing tumour cells", Cell Death and Differentiation., vol. 16, No. 1, Jan. 1, 2009 (Jan. 1, 2009), pp. 184-186, XP55407217, GB ISSN: 1350-9047, DOI: 10.1038/cdd.2008.164.
Reynolds Gary M et al: "Hepatitis C virus receptor expression in normal and diseased liver tissue", Hepatology, Wiley, vol. 47, No. 2, Feb. 1, 2008 (Feb. 1, 2008 ), pp. 418-427, XP002516760.
Stieglmaier Julia et al: "Selective induction of apoptosis in leukemic B-lymphoid cells by a CD19-specific TRAIL fusion protein", Cancer Immunology, Immunotherapy, Springer, Berlin/ Heidelberg, vol. 57, No. 2, Feb. 1, 2008 (Feb. 1, 2008), pp. 233-246, XP002528355, ISSN: 0340-7004, DOI: 10.1007/S00262-007-0370-8 [retrieved on Jul. 31, 2007].
Cao et al., "Targeting Cell Surface (Beta2)-Microglobulin by Pentameric IgM Antibodies," Br. J. Haematol., vol. 154, (2011), pp. 111-121.
Chames et al. "Selection of Antibodies Against Biotinylated Antigens" Methods in Molecular Biology 2002, 178:147-159.
Chomczynski et al. "Single-Step Method of RNA Isolation by Acid Guanidinium Thiocyanate-Phenol-Chloroform Extraction" Anal. Biochem 1987. 162: 156-159.
Japanese Decision of Refusal for Japanese Application No. 2017-232042, dated Aug. 26, 2019, 9 pages with English Translation.
Japanese Written Opinion for Japanese Application No. 2017-232042, dated Mar. 4, 2019, 10 pages with English Translation.
Mattes et al., "Induction of Apoptosis by Cross-Linking Antibodies Bound to Human B-Lymphoma Cells: Expression of Annexin V Binding Sites on the Antibody Cap," Cancer Biotherapy and Radiopharmaceuticals, vol. 24, (2009), pp. 185-193.

(56) References Cited

OTHER PUBLICATIONS

Pedersen et al., "MHC-I-Induced Apoptosis in Human B-Lymphoma Cells is Dependent on Protein Tyrosine and Serine/Threonine Kinases," Experimental Cell Research, vol. 251, (1999), pp. 128-134.
Riechmann et al. "Single domain antibodies: comparison of camel VH and camelised human VH domains" Journal of Immunological Methods 1999, 231:25-38.
Traversari et al. "A Nonapeptide Encoded by Human Gene MAGE-1 Is Recognized on HLA-A1 by Cytolytic T Lymphocytes Directed against Tumor Antigen MZ2-E" J. Exp. Med 1992, 176:1453-1457.
Wallen-Ohman et al., "A Cell Surface Antigen (BAL) Defined by a Mouse Monoclonal Antibody Inducing Apoptosis in a Human Lymphocytic Leukemia Cell Line," Int. J. Cancer, vol. 57, (1994), pp. 544-552.
Yang et al., "Killing Tumor Cells Via Their Surface (Beta2)M or MHC class I Molecules,"Cancer, vol. 116, (2010), pp. 1638-1645.
Arakawa et al., "Cloning and Sequencing of the VH and V Kappa Genes of an anti-CD3 Monoclonal Antibody, and Construction of a Mouse/Human Chimeric Antibody", j. Biochem, vol. 120, No. 3, (1996), pp. 657-662.
Engler et al; (Vaccine, 2004, p. 58-68).
Park et al, "Expression of MAGE-A and NY-ES0-1 in Primary and Metastatic Cancers" J Immunother. Jan. 2016; 39(1): 1-7.

* cited by examiner

MAGE-A expression in human prostate cancer cell lines and prostate cancer xenografts.

|  | MAGE- | | | | | | | | | | | |
|---|---|---|---|---|---|---|---|---|---|---|---|---|
| Cell line / Xenograft | A1 | A2 | A3 | A4 | A5 | A6 | A7 | A8 | A9 | A10 | A11 | A12 |
| LNCaP | + | ++ | ++ |  |  | ++ | + |  |  |  |  |  |
| PC346C | + | ++ | ++ | + |  | ++ | + |  |  | + | ++ |  |
| OVCAR |  |  | + | + |  | + |  |  |  | + |  |  |
| JON |  |  | ++ | ++ |  | ++ |  |  |  | + | + |  |
| PNT 2 C2 |  |  | + | + |  | + |  |  |  | + | + |  |
| SD48 |  |  |  | + |  | + |  |  |  | + | + |  |
| PC-3 |  |  |  |  |  | + |  |  |  | + | + |  |
| PC 374 |  | + |  |  |  |  |  |  |  |  |  |  |
| PC 346p | + | ++ | ++ |  |  | ++ |  |  |  | + | ++ | + |
| PC 82 |  |  | + | + |  |  |  |  |  |  |  |  |
| PC 133 | ++ | + |  |  |  |  |  |  | + |  |  |  |
| PC 135 | + |  |  |  |  |  |  |  |  |  |  |  |
| PC 295 | + |  |  |  |  |  |  |  |  |  |  |  |
| PC 324 |  |  | + |  |  | + |  |  | + |  |  |  |
| PC 310 | + | ++ |  | + |  | ++ |  |  |  |  |  | + |
| PC 339 |  | ++ | ++ |  | + | ++ |  | + | + |  |  | + |

Expression of the MAGE-A1, A2, A3, A4, A5, A6, A7, A8, A9, A10, A11 and A12 genes in diverse prostate tumor cell lines and prostate xenografts was analyzed by RT-PCR. Shown are expression levels in individual samples tested. Blank= no expression, + = low expression, ++ = high expression.

All cell lines / xenografts express at least one MAGE-A gene.

*FIG. 8*

ABERRANT CELL-RESTRICTED IMMUNOGLOBULINS PROVIDED WITH A TOXIC MOIETY

CROSS-REFERENCE TO RELATED APPLICATIONS

This application is a national phase entry under 35 U.S.C. § 371 of International Patent Application PCT/NL2013/050014, filed Jan. 11, 2013, designating the United States of America and published in English as International Patent Publication WO2013/105856 A1 on Jul. 18, 2013, which claims the benefit under Article 8 of the Patent Cooperation Treaty to U.S. Ser. No. 61/586,568, filed Jan. 13, 2012.

TECHNICAL FIELD

The disclosure relates to the field of biotherapeutics. More specifically, the disclosure relates to immunoglobulins provided with a toxic moiety. Even more specifically, the disclosure relates to human antibodies. The disclosure also relates to the use of these biotherapeutics in the treatment of a host suffering from a disease associated with aberrant cells, such as cancers and autoimmune diseases.

BACKGROUND

The development of immunoglobulin-drug conjugates is one of the drug development fields that receives high attention nowadays. Humanized or human antibodies are the largest and most important class of immunoglobulins under investigation for use in antibody-drug conjugates (ADCs) and in immunotoxins and antibody-radionuclide conjugates. These antibodies target binding sites (over)expressed at aberrant cells, such as those exposed in cancers and (auto) immune diseases, and during infections. Many of the conjugates have a limited degree of efficacy. For example, the maximum tolerated dose of immunotoxins is relatively low due to their toxicity towards healthy tissue. Lowering the dose is one way of protecting healthy cells for the non-specific toxic activity of the toxin or the drug in ADCs. Lowering the dose, however, hampers the delivery of an efficacious amount of conjugate at the site of, for example, a tumor. The unwanted side reactions are mainly due to the targeting of the antibodies to binding sites that are not exclusively exposed by aberrant cells but also to some extent by healthy cells. Thus, insufficient specificity for aberrant cells over healthy cells hampers desired efficacy and hampers obtaining the desired safety profiles of the nowadays immunoglobulin-drug conjugates.

Toxic moieties currently in the clinic or under investigation are numerous and diverse [6]. Amongst the first toxins that were chemically linked to murine antibodies are plant derived protein toxins and bacterial toxins such as saporin, Diphtheria toxin, *Pseudomonas* exotoxin, gelonin, ricin, ricin A chain, abrin and pokeweed antiviral protein. Other immunoglobulins provided with a toxin moiety comprise single chain Fv fused at the DNA level with toxins. An example is the recombinant protein BL22 consisting of the Fv portion of an anti-human CD22 antibody fused to a fragment of *Pseudomonas* exotoxin-A, that targets B-cell malignancies such, as hairy cell leukemia and non-Hodgkin's lymphoma. Other examples of immunoglobulins conjugated to toxins are the antibody-radionuclide conjugates. Human CD20 has been chosen by drug developers as the target for two monoclonal antibodies, conjugated with 90-Yttrium or with 131-Iodine, for treatment of non-Hodgkin's lymphomas. In attempts to improve the tumor selectivity of certain drugs, murine monoclonal antibodies were conjugated to compounds such as doxorubicin, vinblastine, methotrexate, providing so-called antibody-drug conjugates. Insufficient tumor cell specificity, however, still limited the therapeutic usefulness. Even when selecting tumor cell surface antigens that are (highly) over-expressed at aberrant cells, still the low expression levels at healthy cells gives rise to insufficient selectivity of the antibody-drug conjugates. Current cytotoxic anti-tumor drugs under investigation are, for example, maytansinoids and dolastatin analogs, that both target intracellular tubulin, and duocarmycins and calicheamicins, that target DNA structure. These compounds are potent in their cytotoxic activity, though not selective for aberrant cells. Antibiotic calicheamicin conjugated to an anti-human CD33 monoclonal antibody was approved and used in the clinic, but was withdrawn due to serious side effects. Additional examples of drugs currently under investigation for their potential beneficial use in antibody-drug conjugates meant for the treatment of cellular aberrancies are ozogamicin, hydrazone-calicheamicin, vedotin, emtansine, mertansine. These toxic moieties are conjugated to immunoglobulins targeting cell surface markers expressed at tumor cells, though also expressed to some extent at healthy cells. Typical examples of immunoglobulin-drug conjugate-targeted cell surface markers present at both tumor cells and healthy cells are CD19, CD20, CD22, CD25, CD30, CD33, CD56, CD70, HER2/neu. All these immunoglobulin-drug conjugate development programs, thus, inherently bear the risk for unacceptable safety profiles and consequent poor efficacy due to low maximum tolerated doses. Conjugating drugs, radionuclides or toxins to immunoglobulins specifically and selectively targeting aberrant cells and not targeting healthy cells would thus provide for therapies with improved specificity and selectivity for aberrant cells and with an improved safety profile.

SUMMARY OF THE DISCLOSURE

Specific and selective delivery of a toxic moiety in target aberrant cells demands for binding molecules specific for binding sites preferentially associated with aberrant cells. These binding molecules then are used as carriers and transporters of the toxic moieties, specifically and selectively delivering the toxic moieties at and in the aberrant cells. We here disclose immunoglobulin-drug conjugates comprising these preferred features. The immunoglobulins in the immunoglobulin-drug conjugates of the disclosure comprise immunoglobulin binding regions with improved selectivity for aberrant cells by specifically binding to binding sites preferentially associated with these aberrant cells. We disclose as preferred targets for the antibody of the disclosure, intracellular proteins that are associated with aberrant cells. These proteins are available as peptides presented by MHC on the surface of aberrant cells. The use of MHC-peptide complexes as targets opens us a new field of tumor targets, because so far, typically, targets associated with the surface of aberrant cells have been envisaged. Although it is preferred that the target is specific for aberrant cells (tumor cells) in many cases upregulated intracellular proteins are also suitable for at least improving the therapeutic window of immunotoxins. Our most preferred targets are peptides derived from MAGE presented in the context of MHC-1. In particular, MAGE peptides that are present in more than one MAGE protein (multi-MAGE epitope; see WO2012/091564 incorporated herein by reference). The toxic moiety, according to the disclosure, is preferably a drug compound, a radionuclide or a toxin. The toxic moiety, according to the disclosure, is a non-proteinaceous molecule or a proteinaceous molecule. In the immunoglobulin-drug conjugates of the disclosure, the toxic moiety is preferably conjugated by chemical conjugation. Also preferred are immunoglobulins of the disclosure fused at the DNA level to a proteinaceous toxic moiety.

The immunoglobulins in the immunoglobulin-drug conjugates of the disclosure are suitable for the specific and selective localization of a toxic effect inside targeted aberrant cells, leaving healthy cells essentially unaffected. Immunoglobulins comprise immunoglobulin binding domains, referred to as immunoglobulin variable domains, comprising immunoglobulin variable regions. Maturation of immunoglobulin variable regions results in variable domains adapted for specific binding to a target binding site. Immunoglobulins are, therefore, particularly suitable for providing the immunoglobulin-drug conjugates of the disclosure with the ability to specifically and selectively target aberrant cells. At their surface, aberrant cells present aberrant cell-associated antigen peptides in the context of major histocompatibility complex (MHC). Therefore, for the immunoglobulins in the immunoglobulin-drug conjugates of the disclosure, aberrant cell-associated MHC-1 peptide complexes are a preferred target on aberrant cells. In addition, aberrant cell-associated MHC-2 peptide complexes are valuable targets on, e.g., tumors of hematopoietic origin, for the immunoglobulins in the immunoglobulin-drug conjugates of the disclosure. The disclosure, therefore, provides immunoglobulins in immunoglobulin-drug conjugates, with improved specificity and selectivity for aberrant cells by targeting MHC-peptide complexes, which are preferentially associated with aberrant cells. This improved specificity and selectivity for aberrant cells is accompanied with a reduced level of unintentional targeting of healthy cells by the immunoglobulins in the immunoglobulin-drug conjugates of the disclosure. Most preferably, healthy cells are not targeted by the immunoglobulin-drug conjugates of the disclosure. Thus, in a first embodiment, the disclosure provides an immunoglobulin provided with a toxic moiety, comprising at least an immunoglobulin variable region that specifically binds to an MHC-peptide complex preferentially associated with aberrant cells. Preferred immunoglobulins of the disclosure are antibodies, but fragments and/or derivatives such as Fab and/or ScFv can also be used. Even more preferred immunoglobulins of the disclosure are antibodies of the immunoglobulin G (IgG) type. Other immunoglobulins of the disclosure are, for example, heavy-chain (only) antibodies comprising Vh or Vhh and IgA, and their fragments such as Fab fragments, and Fab fragments of IgG's. Immunoglobulins bind via their immunoglobulin variable regions to binding sites on molecules, such as epitopes, with a higher binding affinity than background interactions between molecules. In the context of the disclosure, background interactions are typically interactions with an affinity lower than a $K_D$ of 10E-4 M. Immunoglobulin variable domains in light chains (Vl) and immunoglobulin variable domains in heavy chains (Vh) of antibodies typically comprise the aberrant-cell specific immunoglobulin variable regions of the disclosure. Thus, in one embodiment, the disclosure provides an immunoglobulin provided with a toxic moiety, comprising at least an immunoglobulin variable region, wherein the immunoglobulin variable region is a Vh(h) that specifically binds to an MHC-peptide complex preferentially associated with aberrant cells. Thus, in yet another embodiment, the disclosure also provides an immunoglobulin provided with a toxic moiety, comprising at least an immunoglobulin variable region, wherein the immunoglobulin variable region is a Vh that specifically binds to an MHC-peptide complex preferentially associated with aberrant cells, and wherein the immunoglobulin variable region further comprises a Vl.

As said, immunoglobulins G are particularly suitable binding molecules for use in therapies specifically and selectively targeting aberrant cells, for site-specific delivery of a toxic moiety, according to the disclosure. Because the anticipated predominant use of the antibodies of the disclosure is in therapeutic treatment regimes meant for the human body, in a particular embodiment of the disclosure, the immunoglobulins provided with a toxic moiety have an amino-acid sequence of human origin. Thus, in one embodiment, the disclosure provides a human IgG provided with a toxic moiety, comprising at least an immunoglobulin variable region, wherein the immunoglobulin variable region is a Vh that specifically binds to an MHC-peptide complex preferentially associated with aberrant cells, and wherein the immunoglobulin variable region further comprises a Vl. Of course, humanized antibodies, with the precursor antibodies encompassing amino acid sequences originating from other species than human, are also part of the disclosure. Also part of the disclosure are chimeric antibodies, comprising (parts of) an immunoglobulin variable region, according to the disclosure, originating from a species other than human, and grafted onto a human antibody.

An aberrant cell is defined as a cell that deviates from its healthy normal counterparts. Aberrant cells are, for example, tumor cells, cells invaded by a pathogen such as a virus, and autoimmune cells.

Thus, in one embodiment, the disclosure provides an immunoglobulin according to any of the aforementioned embodiments, wherein the MHC-peptide complex is specific for aberrant cells.

In the molecules of the disclosure, the toxic moieties are preferably chemically linked to the immunoglobulins via any linker chemistry know in the art, and optionally via an additional spacer. According to the disclosure, one or several, preferably two to six toxic moiety molecules are chemically linked to an immunoglobulin molecule of the disclosure. The number of conjugated toxic moiety molecules per single immunoglobulin molecule is restricted by boundaries such as the number of available sites for conjugation on the immunoglobulin, the stability of the conjugate, the preservation of the ability of the immunoglobulin to specifically bind to an aberrant cell, etc. Of course, also two, three, etc., different toxic moieties can be linked to an immunoglobulin, depending amongst others on available binding sites and the applied linker chemistry. Chemical linking of the toxic moieties has several advantages when working with immunoglobulins. This way, toxic moieties cannot interfere with expression, folding, assembly and secretion of the immunoglobulin molecules. Thus, in one embodiment, the disclosure provides an immunoglobulin according to any of the aforementioned embodiments, wherein the toxic moiety is chemically linked to the immunoglobulin. It is then also part of the current disclosure that toxic moieties are covalently bound via peptide bonds, and preferably via a peptide linker, to the immunoglobulins of the disclosure. The toxic moiety and the immunoglobulin are then fused at the DNA level. Thus, in one embodiment, the disclosure provides an immunoglobulin according to any of the aforementioned embodiments, wherein the toxic moiety is a protein, preferably fused to the immunoglobulin at the DNA level, preferably through a linker sequence. In many instances, a simple Gly-Ser linker of 4-15 amino-acid residues may suffice, but if greater flexibility between the immunoglobulin and the toxic moiety is desired longer or more complex linkers may be used. Preferred linkers are (Gly$_4$Ser)$_n$, (GlySerThrSerGlySer)$_n$, GlySerThrSerGlySerGlyLysProGlySerGlyGluGlySerThrLysGly [SEQ ID. NO:108], GlyPheAlaLysThrThrAlaProSerValTyrProLeuAlaProValLeuGluSerSerGlySerGly [SEQ ID NO:109] or any other linker that provides flexibility allowing protein folding, stability against undesired proteolytic activity and flexibility for the immunoglobulins of the disclosure to exert their activity. Another group of preferred linkers are linkers based on hinge regions of immunoglobulins. These linkers tend to be quite flexible and quite resistant to proteases. The most preferred linkers based on hinge regions are GluProLysSerCysAspLysThrHisThr [SEQ ID NO:110] (linking Ch1 and Ch2 in IgG1), GluLeuLysThrProLeuGlyAspThrThrHisThr [SEQ ID NO:111] (IgG3), and GluSerLysTyrGlyProPro [SEQ ID NO:112] (IgG4). Thus, the role of any applied chemical linker in conjugates, according to the disclosure, or the role of any applied peptide linker in fused molecules, according to the disclosure, is aiding the dual activity of the antibodies of the disclosure, i.e., specific and selective binding of the immunoglobulin to aberrant cells, and subsequent delivery of at least the toxic moiety in the targeted aberrant cells. Thus, in one embodiment, the disclosure provides the use of an immunoglobulin provided with a toxic moiety, according to any of the aforementioned embodiments, for the treatment of a host suffering from a disease associated with aberrant cells. In a further embodiment, the disclosure provides the use of an immunoglobulin provided with a toxic moiety, according to any of the aforementioned embodiments, for the treatment of a host suffering from a disease associated with aberrant cells, wherein at least the toxic moiety is internalized into the aberrant cell. According to the disclosure, the immunoglobulins provided with a toxic moiety are, for example, used for the treatment of cancer. Thus, in a preferred embodiment, the disclosure provides an immunoglobulin provided with a toxic moiety, according to any of the aforementioned embodiments for use in the treatment of cancer.

Preferred toxic moieties, according to the disclosure, are numerous. Several examples of preferred toxic moieties, according to the disclosure, are drugs such as doxorubicin, cisplatin, carboplatin, vinblastine, methotrexate, chelated radioactive metal ions, (synthetic) antineoplastic agents such as monomethyl auristatin E, radioactive iodine, radionuclides such as 90-Yttrium, 131-Iodine, to name a few, which are chemically conjugated to the immunoglobulins of the disclosure. Also, preferred toxic moieties, according to the disclosure, are proteinaceous toxins such as a fragment of *Pseudomonas* exotoxin-A, statins, ricin A, gelonin, saporin, interleukin-2, interleukin-12, viral proteins E4orf4, apoptin and NS1, and non-viral proteins HAMLET, TRAIL and mda-7. Thus, in one embodiment of the disclosure, antibodies are provided for the specific targeting of aberrant cells, wherein the toxic moiety is selected from the list of available toxic moieties comprising toxins such as a fragment of *Pseudomonas* exotoxin-A, statins, chelated radioactive metal ions, radioactive iodine, ricin A, gelonin, saporin, interleukin-2, interleukin-12, radionuclides such as 90-Yttrium, 131-Iodine, drugs such as doxorubicin, taxol or derivatives, 5-FU, anthracyclines, *vinca* alkaloids, calicheamicins, cisplatin, carboplatin, vinblastine, methotrexate, (synthetic) antineoplastic agents such as monomethyl auristatin E, apoptin, parvovirus-H1 NS1 protein, E4orf4, TRAIL, mda-7, HAMLET.

According to the disclosure, proteinaceous molecules are molecules comprising at least a string of amino acid residues. In addition, according to the disclosure, the proteinaceous molecules may comprise carbohydrates, disulphide bonds, phosphorylations, sulphatations, etc.

When antibodies of the disclosure are designed to first bind to a target aberrant cell, followed by internalization, the toxic moiety can then, subsequently, have its intracellular (cytotoxic) function, i.e., inducing apoptosis.

For administration to subjects, the antibodies of the disclosure, must be formulated. Typically, these antibodies will be given parenterally. For formulation simply water (saline) for injection may suffice. For stability reasons more complex formulations may be necessary. The disclosure contemplates lyophilized compositions as well as liquid compositions, provided with the usual additives. Thus, in one embodiment, the disclosure provides a pharmaceutical composition comprising an immunoglobulin provided with a toxic moiety, according to any of the aforementioned embodiments and suitable diluents and/or excipients.

The dosage of the antibodies of the disclosure must be established through animal studies, (cell-based) in vitro studies and clinical studies in so-called rising-dose experiments. Typically, the doses will be comparable with present day antibody dosages (at the molar level). Typically, such dosages are 3-15 mg/kg body weight, or 25-1000 mg per dose.

In addition, especially in the more difficult to treat cellular aberrancies, the first applications of the antibodies of the disclosure will, at least initially, probably take place in combination with other treatments (standard care). Of course, the disclosure also provides antibodies for use in novel or first treatments of any malignancy accompanied by the occurrence of aberrant cells, for which current treatments are not efficient enough or for which currently no treatment options are available. Thus, for example, the disclosure also provides a pharmaceutical composition comprising an invented immunoglobulin provided with a toxic moiety and a conventional cytostatic and/or tumoricidal agent. Moreover, the current disclosure also provides a pharmaceutical composition comprising an invented immunoglobulin provided with a toxic moiety for use in an adjuvant treatment of cancer. Thus, in one embodiment of the disclosure, an invented immunoglobulin provided with a toxic moiety for use in an adjuvant treatment of cancer is provided. Additionally, the current disclosure also provides a pharmaceutical composition comprising an invented immunoglobulin provided with a toxic moiety for use in a combination chemotherapy treatment of cancer. Examples of chemotherapeutical treatments that are combined with the pharmaceutical composition of the current disclosure are etoposide, paclitaxel, cisplatin, doxorubicin and methotrexate.

The pharmaceutical compositions, according to the disclosure, will typically find their use in the treatment of cancer, particularly in forms of cancer where the targets of the preferred antibodies of the disclosure (complexes of MHC and tumor-specific antigen peptides) are presented by the tumors. Table 1, for example, gives a list of tumors on which complexes of WIC and MAGE-A peptides have been found. It is easy using an antibody of the disclosure to identify tumors that present these target MHC-peptide complexes. This can be done in vitro or in vivo (imaging).

It is preferred that the cell-surface molecules comprising the binding sites for the antibodies of the disclosure are internalized into the targeted aberrant cell, together with the antibodies of the disclosure, or together with at least the toxic moiety of the antibodies of the disclosure. In a particularly preferred embodiment of the disclosure, the targeted aberrant cells go into apoptosis as a result of the internalization. Thus, in one embodiment, the disclosure provides the use of an immunoglobulin provided with a toxic moiety, according to any of the aforementioned embodiments, for the treatment of a host suffering from cancer, wherein at least the toxic moiety is internalized into the aberrant cell.

The disclosure, of course, also comprises a nucleic acid molecule encoding the immunoglobulin part of an antibody, according to any of the embodiments of the disclosure, when the toxic moiety is chemically linked to the immunoglobulin in the antibody of the disclosure. Thus, the disclosure also comprises a nucleic acid molecule encoding an immunoglobulin and a toxic moiety, according to any of the embodiments of the disclosure, when the toxic moiety is fused to the immunoglobulin at the DNA level. These molecules, according to the disclosure, can be produced in prokaryotes or eukaryotes. The codon usage of prokaryotes may be different from that in eukaryotes. The nucleic acids, according to the disclosure, can be adapted in these respects. Also, elements that are necessary for secretion may be added, as well as promoters, terminators, enhancers, etc. Also, elements that are necessary and/or beneficial for the isolation and/or purification of the immunoglobulins of the disclosure, or of the antibodies of the disclosure, may be added. Typically, the nucleic acids, according to the disclosure, are provided in an expression vector suitable for the host in which they are to be produced. Choice of a production platform will depend on the size of the molecule, the expected issues around protein folding, whether amino-acid sequences are present in the immunoglobulin or in the antibody that requires glycosylation, expected issues around isolation and/or purification, etc. For example, the presence of disulfide bonds in immunoglobulins or proteinaceous toxins of the disclosure will typically guide the selection of the preferred production platform. Thus, typically nucleic acids, according to the disclosure, are adapted to the production and purification platform in which the immunoglobulins optionally with their fused proteinaceous toxins of the disclosure are to be produced. Thus, the disclosure provides a vector comprising a nucleic acid molecule encoding an immunoglobulin or an antibody of the disclosure. For stable expression in a eukaryote, it is preferred that the nucleic acid encoding the immunoglobulin, or the antibody of the disclosure is integrated in the host cell genome (at a suitable site that is not silenced). In one embodiment, the disclosure, therefore, comprises: a vector comprising means for integrating the nucleic acid in the genome of a host cell. The disclosure further comprises the host cell or the organism in which the nucleic acid molecule encoding for the immunoglobulin of the disclosure, optionally with their fused proteinaceous toxins, is present and which is thus capable of producing the immunoglobulin, optionally with their fused proteinaceous toxins of the disclosure. Thus, in a preferred embodiment, the disclosure comprises a cell comprising a nucleic acid molecule, according to the disclosure, preferably integrated in its genome and/or a vector, according to the disclosure, comprising a nucleic acid molecule encoding an immunoglobulin optionally with their fused proteinaceous toxins of the disclosure.

Included in the disclosure is also a method for producing an immunoglobulin optionally with their fused proteinaceous toxins of the disclosure, comprising culturing a cell, according to the disclosure, comprising a nucleic acid molecule encoding an immunoglobulin optionally with their fused proteinaceous toxins of the disclosure, preferably integrated in the cell's genome and/or a vector, according to the disclosure, comprising a nucleic acid molecule encoding an immunoglobulin optionally with their fused proteinaceous toxins of the disclosure, allowing for expression of the immunoglobulin optionally with their fused proteinaceous toxins and separating the immunoglobulin optionally with their fused proteinaceous toxins from the culture.

In one embodiment of the disclosure, the immunoglobulin variable domains in the molecules of the disclosure target one binding site. Also, according to the disclosure, bi-specific immunoglobulins provided with a toxic moiety are provided that are specifically binding to two different binding sites associated with the cell surface of aberrant cells. By targeting with a single antibody of the disclosure two different binding sites on an aberrant cell such as a tumor cell, the risk that both targets are also jointly present on a healthy cell is significantly further diminished. The affinity of the antibodies of the disclosure for the two different target binding sites separately, preferably is designed such that $K_{on}$ and $K_{off}$ are very much skewed towards binding to both different binding sites simultaneously. Thus, the specificity of the bi-specific antibodies of the disclosure is increased by increasing their specificity for binding to two different binding sites associated with aberrant cells. Thus, in one embodiment of the disclosure, the antibody, according to any of the previous embodiments, is a hetero-dimeric bi-specific immunoglobulin G or heavy-chain only antibody comprising two different but complementary heavy chains. The two different but complementary heavy chains may then be dimerized through their respective Fc regions. Upon applying preferred pairing biochemistry, hetero-dimers are preferentially formed over homo-dimers. For example, two different but complementary heavy chains are subject to forced pairing upon applying the "knobs-into-holes" CH3 domain engineering technology as described [Ridgway et al., *Protein Engineering*, 1996 (ref. 14)]. In a preferred embodiment of the disclosure, the two different immunoglobulin variable regions in the bi-specific immunoglobulins of the disclosure specifically bind to an MEC-peptide complex preferentially associated with aberrant cells.

Typical preferred antibodies of the disclosure are exemplified by the antibodies outlined in this section, in FIG. 5, Panel B, and by the examples provided below and in the Examples section. Thus, the disclosure provides an immunoglobulin provided with a toxic moiety, according to FIG. 5, Panel B.

DETAILED DESCRIPTION

One aspect of the disclosure relates to a method for providing the antibodies of the disclosure. As described herein above, it typically involves providing a nucleic acid construct encoding the desired immunoglobulin part of antibodies of the disclosure, or encoding the desired immunoglobulin fused to a proteinaceous toxic moiety. The nucleic acid construct can be introduced, preferably via a plasmid or expression vector, into a prokaryotic host cell and/or in a plant cell and/or in a eukaryotic host cell capable of expressing the construct. In one embodiment, a method of the disclosure to provide an immunoglobulin or to provide an immunoglobulin fused to a proteinaceous toxic moiety, comprises the steps of providing a host cell with the nucleic acid(s) encoding the immunoglobulin or the immunoglobulin fused to a proteinaceous toxic moiety, and allowing the expression of the nucleic acid(s) by the host cell.

It is part of the disclosure that nucleic acids coding for selected (human) immunoglobulin Vh(h) domains, according to any of the above embodiments, are combined with nucleic acids coding for human immunoglobulin heavy chain constant domains, providing nucleic acid molecules of the disclosure encoding for a heavy chain of a human antibody. The human antibody heavy chain protein product of such a nucleic acid molecule of the disclosure then may be hetero-dimerized with a universal human antibody light chain. It is also part of the disclosure that nucleic acids coding for (jointly) selected human immunoglobulin Vl domains and Vh domains, according to any of the above embodiments, are combined with nucleic acids coding for a human immunoglobulin light chain constant domain and are combined with nucleic acids coding for human immunoglobulin heavy chain constant domains, respectively, providing nucleic acid molecules of the disclosure encoding for a light chain and for a heavy chain of a human antibody. In yet another embodiment of the disclosure, the nucleic acids coding for the complementarity determining regions 1, 2 and 3 (CDR1, CDR2, CDR3), forming together the immunoglobulin variable region of a selected immunoglobulin Vh domain and/or a selected immunoglobulin Vl domain, according to any of the above embodiments, are combined with nucleic acids coding for human immunoglobulin Vh domain frame work regions and/or human immunoglobulin Vl domain frame work regions, respectively, providing nucleic acid molecules of the disclosure encoding for a heavy chain variable domain (Vh) of a human antibody and/or encoding for a light chain variable domain (Vl) of a human antibody (a method known in the art as "grafting"). These nucleic acid molecules encoding for variable domains Vh and/or Vl are, as part of the disclosure, then combined with nucleic acids coding for human immunoglobulin constant domains, providing a nucleic acid molecule encoding for a human antibody heavy chain and/or providing a nucleic acid molecule encoding for a human antibody light chain.

According to the disclosure, immunoglobulins or immunoglobulins fused to a proteinaceous toxic moiety are, for example, expressed in plant cells, eukaryotic cells or in prokaryotic cells. Non-limited examples of suitable expression systems are tobacco plants, *Pichia pastoris, Saccharomyces cerevisiae*. Also cell-free recombinant protein production platforms are suitable. Preferred host cells are bacteria, like, for example, bacterial strain BL21 or strain SE1, or mammalian host cells, more preferably human host cells. Suitable mammalian host cells include human embryonic kidney (HEK-293) cells, PerC6 cells or preferably Chinese hamster ovary (CHO) cells, which can be commercially obtained. Insect cells, such as S2 or S9 cells, may also be used using baculovirus or insect cell expression vectors, although they are less suitable when the immunoglobulins or the fused immunoglobulins-toxic moiety molecules, according to the disclosure, include elements that involve glycosylation. The produced immunoglobulins or fused immunoglobulin-toxic moiety molecules, according to the disclosure, can be extracted or isolated from the host cell or, if they are secreted, from the culture medium of the host cell. Thus, in one embodiment, a method of the disclosure comprises providing a host cell with one or more nucleic acid(s) encoding the immunoglobulin or the fused immunoglobulin-toxic moiety molecule, allowing the expression of the nucleic acids by the host cell. In another preferred embodiment, a method of the disclosure comprises providing a host cell with one or more nucleic acid(s) encoding two or more different immunoglobulins or two or more different fused immunoglobulin-toxic moiety molecules, allowing the expression of the nucleic acids by the host cell. For example, in one embodiment, nucleic acids encoding for a so-called universal immunoglobulin light chain and nucleic acids encoding for two or more different immunoglobulin heavy chains are provided, enabling isolation of mono-specific immunoglobulins or mono-specific fused immunoglobulin-toxic moiety molecules comprising homo-dimers of heavy chains and/or enabling isolation of bi-specific immunoglobulins or bi-specific fused immunoglobulin-toxic moiety molecules comprising hetero-dimers of heavy chains, with all different heavy chains complexed with a universal light chain. Methods for the recombinant expression of (mammalian) proteins in a (mammalian) host cell are well known in the art.

As said, it is preferred that the immunoglobulins of the disclosure are linked with the toxic moieties via bonds and/or binding interactions other than peptide bonds. Methods for linking proteinaceous molecules such as immunoglobulins to other proteinaceous molecules or non-proteinaceous molecules are numerous and well known to those skilled in the art of protein linkage chemistry. Protein linkage chemistry not based on peptide bonds can be based on covalent interactions and/or on non-covalent interactions. A typical example of linkage chemistries applicable for linking toxic moieties to immunoglobulins of the disclosure are the various applications of the Universal Linkage System disclosed in patent applications WO92/01699, WO96/35696, WO98/45304, WO03040722.

As will be clear, an antibody of the disclosure finds its use in many therapeutic applications and non-therapeutic applications, e.g., diagnostics, or scientific applications. Antibodies of the disclosure, or more preferably the immunoglobulin part of the antibodies of the disclosure, suitable for diagnostic purposes are of particular use for monitoring the expression levels of molecules exposing binding sites on aberrant cells that are targeted by antibodies of the disclosure. In this way, it is monitored whether the therapy remains efficacious or whether other antibodies of the disclosure targeting one or two different binding sites on the aberrant cells should be applied instead. This is beneficial when the expression levels of the first or the first two targeted binding site(s) are below a certain threshold, whereas another or new binding sites (still) can serve as newly targeted binding sites for antibodies of the disclosure comprising the appropriate specific immunoglobulin variable regions for these alternative binding site(s). Antibodies of the disclosure may also be used for the detection of (circulating) tumor cells, and for the target-cell specific delivery of immune-stimulatory molecules. For these later two uses, the sole immunoglobulins of the disclosure without the fused or conjugated toxic moiety may also be used.

Provided herein is a method for inducing ex vivo or in vivo a modulating effect on a biological process in a target cell, comprising contacting the cell with an antibody of the disclosure in an amount that is effective to induce the modulating effect. Preferably, the antibody of the disclosure is used for a modulating effect on a biological process of aberrant cells in a subject, more preferably a human subject. For therapeutic applications in humans, it is, of course, preferred that an antibody of the disclosure does not contain amino acid sequences of non-human origin. More preferred are antibodies of the disclosure, which only contain human amino acid sequences. Therefore, a therapeutically effective amount of an antibody of the disclosure capable of recognizing and binding to one or two disease-specific binding sites and subsequently inducing a modulating effect on a biological process in the cell, can be administered to a patient to stimulate eradication of aberrant cells expressing the binding site(s) without affecting the viability of (normal)

cells not expressing the disease-specific binding site(s). The specific killing of aberrant cells while minimizing or even avoiding the deterioration or even death of healthy cells will generally improve the therapeutic outcome of a patient after administration of the antibodies of the disclosure.

Accordingly, also provided is the use of an antibody of the disclosure as medicament. In another aspect, the disclosure provides the use of an antibody of the disclosure for the manufacture of a medicament for the treatment of cancer, autoimmune disease, infection or any other disease of which the symptoms are reduced upon targeting aberrant cells expressing disease-specific binding sites with antibodies of the disclosure. For example, an antibody of the disclosure is advantageously used for the Manufacture of a medicament for the treatment of various cancers (e.g., solid tumors, hematologic malignancies).

An example of a preferred antibody of the disclosure is an antibody comprising at least an immunoglobulin variable region specifically binding to the complex between MHC-1 HLA-0201 and a multi-MAGE-A epitope, conjugated with a toxic moiety, using, for example, Universal Linkage System linker chemistry for conjugation. A second example of a preferred antibody of the disclosure is an antibody comprising at least an immunoglobulin variable region specifically binding to the complex between MHC-1 HLA-CW7 and a multi-MAGE-A epitope, conjugated with a toxic moiety, using, for example, Universal Linkage System linker chemistry for conjugation. With the bi-specific antibodies of the disclosure, difficult to target and/or difficult to reach aberrant cells have a higher chance of being "hit" by at least one of the two different immunoglobulin variable regions in the bi-specific antibodies of the disclosure, thereby providing at least in part the therapeutic activity. An example of a preferred bi-specific antibody of the disclosure is an immunoglobulin comprising an immunoglobulin variable region specific for the complex between MHC-1 HLA-0201 and a multi-MAGE-A epitope and comprising a second immunoglobulin variable region specific for the complex between MHC-1 HLA-CW7 and a second multi-MAGE-A epitope, conjugated with a toxic moiety.

Antibody fragments of human origin can be isolated from large antibody repertoires displayed by phages. One aspect of the disclosure, known by the art, is the use of human antibody phage display libraries for the selection of human antibody fragments specific for a selected binding site, e.g., an epitope. Examples of such libraries are phage libraries comprising human Vh repertoires, human Vh-Vl repertoires, human Vh-Ch1 or human antibody Fab fragment repertoires.

Although the disclosure contemplates many different combinations of MHC and antigenic peptides, the most preferred is the combination of MHC-1 and an antigenic peptide from a tumor related antigen presented by the MHC-1, exclusively expressed by aberrant cells and not by healthy cells. Because of HLA restrictions, there are many combinations of MHC-1-peptide complexes as well as of MHC-2-peptide complexes that can be designed based on the rules for presentation of peptides in MHC. These rules include size limits on peptides that can be presented in the context of MHC, restriction sites that need to be present for processing of the antigen in the cell, anchor sites that need to be present on the peptide to be presented, etc. The exact rules differ for the different HLA classes and for the different MHC classes. We have found that MAGE derived peptides are very suitable for presentation in an MHC context. An MHC-1 presentable antigenic peptide with the sequence Y-L-E-Y-R-Q-V-P-G in MAGE-A [SEQ ID NO:3] was identified, that is present in almost every MAGE-A variant (multi MAGE peptide) and that will be presented by one of the most prevalent MHC-1 alleles in the Caucasian population (namely HLA-A0201). A second MAGE peptide that is presented by another MHC-1 allele (namely HLA-CW7) and that is present in many MAGE variants, like, for example, MAGE-A2, -A3, -A6 and -A12, is E-G-D-C-A-P-E-E-K [SEQ ID NQ:4]. These two combinations of MHC-1 and MAGE peptides together would cover 80% of the Caucasian population. The same approach can be followed for other MHC molecules, other HLA restrictions and other antigenic peptides derived from tumor-associated antigens. Relevant is that the chosen antigenic peptide to elicit the response to must be presented in the context of an MHC molecule and recognized in that context only. Furthermore, the antigenic peptide must be derived from a sufficiently tumor specific antigen and the HLA restriction must occur in a relevant part of the population. One of the important advantages of the disclosure is that tumors that down regulate their targeted MHC-peptide complex can be treated with a second immunoglobulin comprising at least one variable region binding to a different MHC-peptide complex based on the same antigen. If this one is down regulated, a third one will be available. For heterozygotes six different targets on MHC-1 may be available. Since cells need to be "inspected" by the immune system from time to time, escape through down regulation of all MHC molecules does not seem a viable escape route. In the case that MAGE is the antigen from which the peptide is derived escape through down regulation of the antigen is also not possible, because MAGE seems important for survival of the tumor [8]. Thus, the disclosure, in an important aspect reduces or even prevents escape of the tumor from the therapy. Thus, the disclosure provides in a preferred embodiment an antibody of the disclosure whereby the immunoglobulin variable region is capable of binding to an MHC-I-peptide complex. In a further preferred embodiment, the disclosure provides an immunoglobulin whereby the immunoglobulin variable region is capable of binding to MHC-I-peptide complexes comprising an antigenic peptide derived from a tumor related antigen, in particular MHC-I-peptide complexes comprising an antigenic peptide present in a variety of MAGE antigens, whereby the immunoglobulin is provided with a toxic moiety.

Because in one embodiment, the disclosure uses MHC molecules as a target, and individuals differ in the availability of MHC targets, the disclosure also provides a so-called companion diagnostic to determine the HLA composition of an individual. Although the disclosure preferably uses a more or less universal (MAGE) peptide, the disclosure also provides a diagnostic for determining the expression of the particular antigen by the tumor. In this manner the therapy can be geared to the patient (personalized medicine, patient stratification), particularly, also in the set-up to prevent escape, as described hereinbefore. It is known that the HLA restriction patterns of the Asian population and the black population are different from the Caucasian population. For different populations different MHC-peptide complexes can be targeted.

Although the present specification presents more specific disclosure on tumors, it must be understood that other aberrant cells can also be targeted by the antibodies of the disclosure. These other aberrant cells are typically cells that also proliferate without sufficient control. This occurs in autoimmune diseases. It is typical that these cells start to show expression of tumor antigens. In particular, MAGE polypeptides have been identified in rheumatoid arthritis [7].

In literature it is shown that a single nine amino-acid (A.A.) peptide in MAGE-A2, -A3, -A4, -A6, -A10, and -A12 is presented by HLA-A0201 on tumor cells, and can be recognized by cytotoxic T-lymphocytes [1]. This nine amino acid residues peptide with sequence Y-L-E-Y-R-Q-V-P-G [SEQ ID NO:3] is almost identical to the HLA-A0201 presented MAGE-A1 peptide Y-L-E-Y-R-Q-V-P-D [SEQ ID NO:5], except for the anchor residue at position 9. Replacement of the anchor residue with Valine results in a 9 amino acid residues peptide with enhanced binding capacity to HLA-A0201 molecules [1]. Human and mouse T-lymphocytes recognizing the Y-L-E-Y-R-Q-V-P-V [SEQ ID NO:6] peptide presented by HLA-0201 also recognize the original MAGE-A Y-L-E-Y-R-Q-V-P-G [SEQ ID NO:3] and Y-L-E-Y-R-Q-V-P-D [SEQ ID NO:5] peptides presented on tumors of distinct origin. As diverse tumors may each express at least one MAGE-A gene, targeting of this so-called multi-MAGE-A epitope includes the vast majority of tumors. As an example, MAGE-A expression in human prostate tumor cell lines and in human xenographs was analyzed and shown to be highly diverse, but in each individual sample tested at least one MAGE-A gene was expressed (FIG. 8), confirming that targeting this multi-MAGE-A epitope serves as a universal HLA-A0201 restricted target for therapy.

Of course, several other multi-MAGE or multi-target epitopes may be designed. In principle, the disclosure contemplates combinations of tumor specific antigen derived MHC presented epitopes in different HLA restrictions of both MHC-I and MHC-II, targeted by immunoglobulins linked to a toxic moiety, to induce apoptosis in aberrant cells. Examples of MHC-MAGE peptide combinations that can be targeted by antibodies of the disclosure are peptide IMPKAGLLI (MAGE-A3) [SEQ ID NO:8] and HLA-DP4 or peptide 243-KKLLTQHFVQENYLEY-258 (MAGE-A3) [SEQ ID NO:9] and HLA-DQ6. Other non-limiting examples of tumor specific complexes of HLA and antigen peptide are: HLA A1-MAGE-A1 peptide EADPTGHSY [SEQ ID NO:10], HLA A3-MAGE-A1 SLFRAVITK [SEQ ID NO:11], HLA A24-MAGE-A1 NYKHCFPEI [SEQ ID NO:12], HLA A28-MAGE-A1 EVYDGREHSA [SEQ ID NO:13], HLA B37-MAGE-A1/A2/A3/A6 REPVTKAEML [SEQ ID NO:14], expressed at aberrant cells related to melanoma, breast carcinoma, SCLC, sarcoma, NSCLC, colon carcinoma (Renkvist, N. et al., Cancer Immunol. Immunother. (2001) V50:3-15 (ref. 13)). Further examples are HLA B53-MAGE-A1 DPARYEFLW [SEQ ID NO:15], HLA Cw2-MAGE-A1 SAFPTTINF [SEQ ID NO:16], HLA Cw3-MAGE-A1 SAYGEPRKL [SEQ ID NO:17], HLA Cw16-MAGE-A1 SAYGEPRKL [SEQ ID NO:18], HLA A2-MAGE A2 KMVELVHFL [SEQ ID NO:19], HLA A2-MAGE-A2 YLQLVFGIEV [SEQ ID NO:20], HLA A24-MAGE-A2 EYLQLVFGI [SEQ ID NO:21], HLA-A1-MAGE-A3 EADPIGHLY [SEQ ID NO:22], FHA A2-MAGE-A3 FLWGPRALV [SEQ ID NO:23], HLA B44-MAGE-A3 MEVDPIGHLY [SEQ ID NO:24], HLA B52-MAGE-A3 WQYFFPVIF [SEQ ID NO:25], HLA A2-MAGE-A4 GVYDGREHTV [SEQ ID NO:26], HLA A34-MAGE-A6 MVKISGGPR [SEQ ID NO:27], HLA A2-MAGE-A10 GLYDGMEHL [SEQ ID NO:28], HLA Cw7-MAGE-A12 VRIGHLYIL [SEQ ID NO:29], HLA Cw16-BAGE AARAVFLAL [SEQ ID NO:30], expressed by, for example, melanoma, bladder carcinoma, NSCLC, sarcoma, HLA A2-DAM-6/-10 FLWGPRAYA [SEQ ID NO:31], expressed by, for example, skin tumors, lung carcinoma, ovarian carcinoma, mammary carcinoma, HLA Cw6-GAGE-1/-2/-8 YRPRPRRY [SEQ ID NO:32], HLA A29-GAGE-3/-4/-5/-6/-7B YYWPRPRRY [SEQ-ID 33], both expressed by, for example, melanoma, leukemia cells, bladder carcinoma, HLA B13-NA88-A MTQGQHFLQKV [SEQ ID NO:34], expressed by melanoma, HLA A2-NY-ESO-1 SLLMWITQCFL [SEQ ID NO:35], HLA A2-NY-ESO-1a SLLMWITQC [SEQ ID NO:36], HLA A2-NY-ESO-1a QLSLLMWIT [SEQ ID NO:37], HLA A31-NY-ESO-1a ASGPGGGAPR [SEQ ID NO:38], the latter four expressed by, for example, melanoma, sarcoma, B-lymphomas, prostate carcinoma, ovarian carcinoma, bladder carcinoma.

The disclosure is further exemplified by the non-limiting Examples provided below.

Abbreviations Used

A.A., amino acid; Ab, antibody; β2-M, CDR, complementarity determining region; CHO, Chinese hamster ovary; CT, cancer testis antigens; CTL, cytotoxic T-lymphocyte; E4orf4, adenovirus early region 4 open reading frame; EBV, Epstein-Barr virus; ELISA, enzyme linked immunosorbent assay; HAMLET, human α-lactalbumin made lethal to tumor cells; HEK, human embryonic kidney; HLA, human leukocyte antigen; Ig, immunoglobulin; i.v., intravenously; kDa, kilo Dalton; MAGE, melanoma-associated antigen; Mda-7, melanoma differentiation-associated gene-7; MHC, major histocompatibility complex; MHC-p, WIC-peptide; NS1, parvovirus-H1 derived non-structural protein 1; PBSM, PBS containing 2% non-fat dry milk; TCR, T-cell receptor; VH, Vh or $V_H$, amino-acid sequence of an immunoglobulin variable heavy domain; Vl, amino-acid sequence of an immunoglobulin variable light domain; TRAIL, tumor necrosis factor-related apoptosis-inducing ligand.

EXAMPLES

Example 1

Non-exhaustive examples of immunoglobulins of the disclosure comprising at least an immunoglobulin variable region that specifically binds to an MHC-peptide complex preferentially associated with aberrant cells or to an aberrant cell surface marker preferentially associated with aberrant cells, with domain topologies as outlined, for example, in FIG. 5, Panel B, are:

Antibodies of the disclosure comprising immunoglobulin variable regions that specifically bind to:

a. a complex comprising a T-cell epitope selected from 146-KLQCVDLHV-154 [SEQ ID NO:74], 141-FLTPKKLQCV-150 [SEQ ID NO:75], 154-VISNDV-CAQV-163 [SEQ ID NO:76], 154-YISNDVCAQV-163 [SEQ ID NO:77] of PSA, presented by HLA-A2 and/or 162-QVHPQKVTK-170 [SEQ ID NO:78] of PSA, presented by HLA-A3, and/or 152-CYASGWGSI-160 [SEQ ID NO:79], 248-HYRKWIKDTI-257 [SEQ ID NO:80] of PSA, presented by HLA-A24, and/or 4-LLHETDSAV-12 [SEQ ID NO:81], 711-ALFDIESKV-719 [SEQ ID NO:82], 27-VLAGGFFLL-35 [SEQ ID NO:83] of PSMA, presented by HLA-A2, and/or 178-NYARTEDFF-186 [SEQ ID NO:84], 227-LYSDPADYF-235 [SEQ ID NO:85], 624-TYSVSFDSL-632 [SEQ ID NO:86] of PSMA, presented by HLA-A24, and/or 299-ALDVYNGLL-307 [SEQ ID NO:87] of PAP, presented by HLA-A2 and/or 213-LYCESVHNF-221 [SEQ ID NO:88] of PAP, presented by HLA-A24 and/or 199-GQDLFGIWSKVYDPL-213 [SEQ ID NO:89], 228-TEDTMTKLRELSELS-242 [SEQ ID NO:90] of PAP, presented by MHC-2 and/or 14-ALQPGTALL-22 [SEQ ID NO:91], 105-AILALLPAL- 113 [SEQ ID NO:92], 7-ALLMAGLAL-15 [SEQ ID NO:93], 21-LLCYSCKAQV-30 [SEQ ID NO:94] of PSCA, presented by HLA-A2 and/or 155-LLANGRM-PTVLQCVN-169 [SEQ ID NO:95] of Kallikrein 4, presented by DRB1*0404 and/or 160-RM-PTVLQCVNVSVVS-174 [SEQ. ID NO:96] of Kallikrein 4, presented by DRB1*0701 and/or 125-SVSESDTIRSISIAS-139 [SEQ ID NO:97] of Kallikrein 4, presented by DPB1*0401, for the treatment of prostate cancer;

b. the HLA B8 restricted epitope from EBV nuclear antigen 3, FLRGRAYGL [SEQ ID NO:98], complexed with MHC I, for the clearance of EBV infected cells;

c. the MAGE-A peptide YLEYRQVPG [SEQ ID NO:3] presented by MHC 1 HLA-A0201, for treatment of cancers accompanied by tumor cells expressing these MHC-peptide complexes (see Table 1);

d. the MAGE-A peptide EGDCAPEEK [SEQ ID NO:4] presented by MHC-1 HLA-CW7, for treatment of cancers accompanied by tumor cells expressing these MHC-peptide complexes (see Table 1);

e. complexes of HLA-A2 and HLA-A2 restricted CD8$^+$ T-cell epitopes, e.g., nonamer peptides FLFLLFFWL [SEQ ID NO:99] (from prostatic acid phosphatase (PAP, also prostatic specific acid phosphatase (PSAP))), TLM-SAMTNL [SEQ ID NO:100] (from PAP), ALDVYNGLL [SEQ ID NO:101] (from PAP), human HLA-A2.1-restricted CTL epitope ILLWQPIPV [SEQ ID NO:102] (from PAP-3), six-transmembrane epithelial antigen of prostate (STEAP), or complexes of HLA-A2.1 and HLA-A2.1-restricted CTL epitope LLLGTIHAL [SEQ ID NO:103] (from STEAP-3), epitopes from mucin (MUC-1 and MUC-2), MUC-1-32mer (CHGVTSAPDTRPAPGSTAPPAHGVTSAPDTRPA [SEQ ID NO:104]), epitopes from Globo H, Lewis$^y$, Tn(c), TF(c) clusters, GM2, prostate-specific membrane antigen (PSMA), Kallikrein 4, prostein, or complexes of HLA-A2.1 and HLA-A2.1-restricted epitopes from BA46, PTH-rP, HER-2/neu, hTERT, and MAGE-A8, for the treatment of prostate cancer;

f. an aberrant cell specific epitope in aberrant cell-specific altered MUC-1 complexed with MHC, or to an aberrant cell specific epitope in aberrant cell-specific altered MUC-1 for, the targeting of aberrant cells in, for example, breast cancer or for the treatment of colorectal cancer;

g. an aberrant cell specific epitope of the aberrant-cell specific epidermal growth factor receptor mutant form vIII complexed with MHC, or to an aberrant cell specific epitope of the epidermal growth factor receptor mutant form vIII, for the treatment of the brain neoplasm glioblastoma multiforme;

h. the complex of MHC with T-cell epitope peptide 369-376 from human Her-2/neu, for the treatment of malignancies related to Her-2 and/or Her-1 over-expression;

i. an epitope of the aberrant-cell specific surface marker CD44 splice variants known as CD44-v6, CD44-v9, CD44-v10, complexed with MHC, or to an aberrant cell specific epitope of an aberrant-cell specific CD44 splice variant, for the treatment of multiple myeloma;

Target binding sites suitable for specific and selective targeting of infected aberrant cells by antibodies of the disclosure are pathogen-derived antigen peptides complexed with MI-IC molecules. Examples of T-cell epitopes of the E6 and E7 protein of human papilloma virus, complexed with indicated HLA molecules, are provided below. Any combination of an HLA molecule complexed with a pathogen-derived T-cell epitope provides a specific target on infected aberrant cells for antibodies of the disclosure. An example of an infected aberrant cell is a keratinocyte in the cervix infected by human papilloma virus (HPV), presenting T-cell epitopes derived from, for example E6 or E7 protein, in the context of MHC. Examples of suitable target HPV 16 E6 T-cell epitopes are peptides FQDPQERPR [SEQ ID NO:39], TTLEQQYNK [SEQ ID NO:40], ISEYRHYCYS [SEQ ID NO:41] and GTTLEQQYNK [SEQ ID NO:42] binding to HLA A1, KISEYRHYC [SEQ ID NO:43] and YCYSIYGTTL [SEQ ID NO:44] binding to HLA A2, LLRREVYDF [SEQ ID NO:45] and IVYRDGNPY [SEQ ID NO:46] binding to HLA A3, TTLEQQYNK [SEQ ID NO:47] binding to HLA A11, CYSLYGTTL [SEQ ID NO:48], KLPQLCTEL [SEQ ID NO:49], HYCYSLYGT [SEQ ID NO:50], LYGTTLEQQY [SEQ ID NO:51], EVYDFAFRDL [SEQ ID NO:52] and VYDFAFRDLC [SEQ ID NO:53] binding to HLA A24, 29-TIHDILLECV-38 [SEQ ID NO:54] binding to HLA A*0201. Equally suitable are HPV 16 E7 T-cell epitopes such as 86-TLGIVCPI-93 [SEQ ID NO:55], 82-LLMGTLGIV-90 [SEQ ID NO:56], 85-GTLGIVCPI-93 [SEQ ID NO:57] and 86-TLGIVCPIC-94 [SEQ ID NO:58] binding to HLA A*0201, HPV 18 E6 T-cell epitopes and HPV 18 E7 T-cell epitopes, binding to HLA A1, A2, A3, A11 or A24. Yet additional examples of T-cell epitopes related to HPV infected cells are HPV E7 derived peptides 1-MHGDTPTLHEYD-12 [SEQ ID NO:59], 48-DRAHYNIVTFCCKCD-62 [SEQ ID NO:60] and 62-DSTLRLCVQSTHVD-75 [SEQ ID NO:61] binding to HLA DR, 7-TLHEYMLDL-15 [SEQ ID NO:62], 11-YMLDLQPETT-20 [SEQ ID NO:63], 11-YMLDLQ-PET-19 [SEQ ID NO:64] and 12-MLDLQPETT-20 [SEQ ID NO:65] binding to HLA A*201, 16-QPETTDLYCY-25 [SEQ ID NO:66], 44-QAEPDRAHY-52 [SEQ ID NO:67] and 46-EPDRAHYNIV-55 [SEQ ID NO:68] binding to HLA B18, 35-EDEIDGPAGQAEPDRA-50 [SEQ ID NO:69] binding to HLA DQ2, 43-GQAE-PDRAHYNIVTFCCKCDSTLRLCVQSTHVDIR-77 [SEQ ID NO:70] binding to HLA DR3, 50-AHYNIVTFCCKCD-62 [SEQ ID NO:71] binding to HLA. DR15, 58-CCKCD-STLRLC-68 [SEQ ID NO:72] binding to HLA DR17 and 61-CDSTLRLCVQSTHVDIRTLE-80 [SEQ ID NO:73] binding to HLA-DRB1*0901.

A good source for selecting binding sites suitable for specific and selective targeting of aberrant cells by antibodies of the disclosure, is the Peptide Database listing T-cell defined tumor antigens and the HLA's binding the T-cell epitopes [9-12; on the World Wide Web at cancerimmunity.org/peptidedatabase/Tcellepitopes.htm]. The database provides combinations of antigen peptides complexed with MHC molecules comprising the indicated class of HLA, unique to tumor cells or over-expressed by tumor cells.

Example 2: Selection of Human Antibody Fragments Specific for HLA-A0201/Multi-MAGE-A To obtain human antibody fragments comprising immunoglobulin variable regions specific for the HLA-A0201 presented multi-MAGE-A epitope Y-L-E-Y-R-Q-V-P-V [SEQ ID NO:6] and FLWGPRALV [SEQ ID NO:23] a Human Fab phage display library was constructed according to the procedure previously described by de Haard et al. (2) and used for selections 1) essentially as described by Chames et al. using biotinylated MHC/p complexes (3), or 2) on cells expressing the relevant antigen.

2.1: Selection of Human Antibody Fragments Specific for HLA-A0201/YLEYRQVPV [SEQ ID NO:6] Using Biotinylated MHC-Peptide Complexes:

Human Fab phages ($10^{13}$ colony forming units) were first pre-incubated for one hour at room temperature in PBS containing 2% non-fat dry milk (PBSM). In parallel, 20 µl Streptavidin-coated beads (DYNAL™) were equilibrated for one hour in PB SM. For subsequent rounds, 100 µl beads were used. To deplete for pan-MHC binders, each selection round, 200 nM of biotinylated MHC class I-peptide (MHC-p) complexes containing an irrelevant peptide (Sanquin, the Netherlands) were added to the phages and incubated for 30 minutes under rotation. Equilibrated beads were added, and the mixture was incubated for 15 minutes under rotation. Beads were drawn to the side of the tube using magnetic force. To the depleted phage fraction, subsequently decreasing amounts of biotinylated MHC-p complexes (200 nM for the first round, and 20 nM for the second and third round) were added and incubated for one hour at room temperature, with continuous rotation. Simultaneously, a pan-MHC class I binding soluble Fab (D3) was added to the phage-MHC-p complex mixture (50, 10, and 5 µg for rounds 1-3, respectively). Equilibrated streptavidin-coated beads were added, and the mixture was incubated for 15 minutes under rotation. Phages were selected by magnetic force. Non-bound phages were removed by 5 washing steps with PBSM, 5 steps with PBS containing 0.1% Tween, and 5 steps with PBS. Phages were eluted from the beads by 10 minutes incubation with 500 µl freshly prepared tri-ethylamine (100 mM). The pH of the solution was neutralized by the addition of 500 µl 1 M Tris (pH 7.5). The eluted phages were incubated with logarithmic growing E. Coli TG1 cells ($OD_{600\ nm}$ of 0.5) for 30 minutes at 37° C. Bacteria were grown overnight on 2×TYAG plates. Next day, colonies were harvested, and a 10 µl inoculum was used in 50 ml 2×TYAG. Cells were grown until an $OD_{600\ nm}$ of 0.5, and 5 ml of this suspension was infected with M13k07 helper phage ($5\times10^{11}$ colony forming units). After 30 minutes incubation at 37° C., the cells were centrifuged, resuspended in 25 ml 2×TYAK, and grown overnight at 30° C. Phages were collected from the culture supernatant, as described previously, and were used for the next round panning. After three selection rounds a 261-fold enrichment was obtained, and 46 out of 282 analyzed clones were shown to be specific for the HLA-A2-multi-MAGE-A complex (FIG. 1). ELISA using the HLA-A0201/multi-MAGE-A complexes as well as HLA-A0201 complexes with a peptide derived from JC virus was used to determine the specificity of the selected Fab.

2.2: Selection of Human Fab Specific for HLA-A0201/FLWGPRALV [SEQ ID NO:23] Using Cells.

Selections of Fab phages specifically binding to HLA-A0201/FLWGPRALV [SEQ ID NO:23] were performed using mouse CMT64 lung tumor cells. To obtain CMT64 cells stably expressing HLA-A0201/FLWGPRALV [SEQ ID NO:23] (A2/FLW) complexes, the CMT64 cells were retroviral infected with a vector encoding a single chain peptide-132M-HLA-A0201 heavy chain construct [SEQ ID No:105]. Human Fab phages ($10^{13}$ colony forming units) were first pre-incubated for one hour at room temperature in PBS containing 2% FCS (PB SF). In parallel, $1.0\times10^6$ CMT64-A2/FLW cells were equilibrated for one hour in PBSF. The phages were first incubated for one hour with $10\times10^6$ CMT 64 cells expressing HLA-A0210/YLEYRQVPG [SEQ ID NO:3] to deplete non-specifically binding phages. The non-bound fraction was then incubated (1 hr at 4° C.) with HLA-A0201/FLWGPRALV [SEQ ID NO:23] expressing CMT64 cells. After extensive washing, bound phages were eluted by adding 500 µl freshly prepared tri-ethylamine (100 mM). The pH of the solution was neutralized by the addition of 500 µl 1 M Tris (pH 7.5). The eluted phages were incubated with logarithmic growing E. Coli TG1 cells ($OD_{600\ nm}$ of 0.5) for 30 minutes at 37° C. Bacteria were grown overnight on 2×TYAG plates. Next day, colonies were harvested. After four rounds of selection individual clones were selected and tested for specificity of binding.

2.3: Human Fab Specific for HLA-A0201/Multi-MAGE-A Epitopes Bind Antigen Positive Cells.

Multi-MAGE-A; Y-L-E-Y-R-Q-V-P-V [SEQ ID NO:6]

Fab phages were analyzed for their capacity to bind HLA-A0201 positive EBV-transformed B-LCL loaded with the multi-MAGE-A peptide Y-L-E-Y-R-Q-V-P-V [SEQ ID NO:6]. The B-LCL line BSM ($0.5\times10^6$) was loaded with multi-MAGE-A peptide (10 µg in 100 µl PBS) for 30 minutes at 37° C., followed by incubation with the Fab phages AH5, CB1, CG1, BD5 and BC7 and analyzed by flow-cytometry. As shown in FIG. 2, Fab AH5, CB1 and CG1, specifically bound to the peptide loaded cells only, whereas Fab BD5 and BC7 displayed non-specific binding to BSM that was not loaded with the multi-MAGE-A peptide. No binding was observed by AH5, CB1 and CG1 to non-peptide loaded cells.

Phages presenting AH5, CB1 and CG1, as well as the HLA-A0101/MAGE-A1 specific Fab phage G8 (4) were then used to stain tumor cell lines of distinct histologic origin. To this end prostate cancer cells (LNCaP), multiple myeloma cells (MDN), melanoma cells (MZ2-MEL43 and G43), and breast cancer cells (MDA-MB157) were stained and analyzed by flow cytometry (FIG. 3). The Fab AH5 specifically bound multiple myeloma cells MDN, and not the HLA-A0201 negative melanoma and breast cancer cells. Both CB1 and CG1 displayed non-specific binding on the melanoma cell line G43. The positive control Fab G8 demonstrated binding to all cell lines tested.

Multi-MAGE-A: F-L-W-G-P-R-A-L-V [SEQ ID NO:23]

To determine the cell-binding capacity of the HLA-A0201/FLWGPRALV selected Fab clone F9 soluble Fab fragments were made by induction of TG-1 bacteria. TG-1 containing pCes-F9 were grown until OD=0.8 and Fab production was induced by addition of 1 mM IPTG. After 13 hours induction the bacterial periplasmic fraction was isolated and dialyzed overnight. Next day soluble Fab F9 fragments were purified by IMAC.

Purified Fab F9 was added to $0.5\times10^6$ CMT 64 cells expressing either HLA-A0210/YLEYRQVPG [SEQ ID NO:3], HLA-A0201/FLWGPRALV [SEQ ID NO:23], or CMT 64 cells that do not express human HLA. As shown in FIG. 6 the Fab clone F9 specifically binds HLA-A0201/FLWGPRALV [SEQ ID NO:23] expressing CMT64 cells and not CMT 64 cells that do not express human HLA or that do express the irrelevant HLA-A0201/YLEYRQVPG [SEQ ID NO:3] molecules.

2.4: Fab AH5 Binds HLA-A0201/Multi-MAGE-A Complexes Only.

ELISA using multiple peptide/MHC complexes then confirmed the specificity of Fab-AH5. To this end HLA-A0201 complexes presenting peptides multi-MAGE-A, gp100, JCV and MAGE-C2, as well as a HLA-A1/MAGE-A1 complex were immobilized on 96 well plates and incubated with phages displaying Fab AH5 and control Fab G8. As shown in FIG. 4, AH5 only binds HLA-A0201/multi-MAGE-A and not the irrelevant complexes HLA-A0201/gp100, HLA-A0201/MAGE-C2, HLA-A0201/JCV and HLA-A0101/

MAGE-A1. The positive control Fab G8 only binds to its relevant target HLA-A0101/MAGE-A1.

The nucleic acids encoding for the HLA-A0201-multi-MAGE-A complex binding Fab AH5 will be combined with nucleic acids encoding for human antibody Ch2-Ch3 domains, providing nucleic acid molecules encoding for a human antibody light chain encompassing the selected Cl-Vl encoding nucleic acids and encoding for a human antibody heavy chain encompassing the selected Ch-Vh encoding nucleic acids. These nucleic acid molecules encoding the desired immunoglobulin will be introduced, via a plasmid or via an expression vector, into a eukaryotic host cell such as a CHO cell. After expression of the immunoglobulin, it will be isolated from the cell culture and purified. Then, a selected toxic moiety will be linked to the immunoglobulin, for example, using Universal Linkage System linker chemistry.

Example 3: Cell Binding and Internalization of an Immunoglobulin Provided with a Toxic Moiety Binding capacity of an antibody of the disclosure is analyzed by flow-cytometry. For example, an antibody comprising immunoglobulin variable regions specific for complexes of HLA-A0201 and the multi-MAGE-A peptide is analyzed. HLA-A0201/multi-MAGE-A positive tumor cells (Daju, MDN and mel 624) and HLA-A0201/multi-MAGE-A negative cells (BSM, G43 and 293) are incubated on ice with purified antibody and detected by addition of fluorescently labeled antibodies. Cells bound by the antibody are quantified and visualized by flow-cytometry. Internalization of antibody is analyzed by confocal microscopy. To this end cells are incubated with the antibody, kept on ice for 30 minutes to allow binding but no internalization. Next, fluorescently labeled antibodies specific for the antibody are added. To induce internalization cells are transferred to 37° C. and fixed with 1% PFA after 5, 10 and 15 minutes.

Example 4: Apoptosis Induction by Antibodies of the Disclosure in Diverse Tumor Cells 4.1: Killing of Diverse Tumor Cells by Immunoglobulin Provided with a Toxic Moiety.

Antibodies of the disclosure are analyzed for their capacity to induce apoptosis by incubation with diverse tumor cells, known to express the antigens comprising the binding sites for the immunoglobulin variable regions. For example, an antibody comprising immunoglobulin variable region VH specific for complexes of HLA-A0201 and the multi-MAGE-A peptide, AH5-BTX, is coupled to a synthetic HPMA polymer containing the BTX peptide and Doxorubicin (as we described in WO2009131435) and analyzed. To this end antibodies of the disclosure coupled to doxorubicin are analyzed for their capacity to induce apoptosis by incubation with diverse tumor cells known to express both HLA-A0201 and MAGE-A genes. The cell-lines Daju, Mel 624 (melanoma), PC346C (prostate cancer), and MDN (multiple myeloma) as well as MAGE-A negative cells (911 and HEK293T) are incubated with different concentrations of the antibodies of the disclosure (in DMEM medium, supplemented with pen/strep, Glutamine and non-essential amino acids). Several hours later, cells are visually inspected for classical signs of apoptosis such as detachment of the cells from tissue culture plates and membrane blebbing. In addition, cells are stained for active caspase-3 to demonstrate apoptosis. It is accepted that the antibodies of the disclosure induce apoptosis in the Daju Mel 624, PC346C and MDN cells. Cells that are not treated with the antibodies of the disclosure are not affected, as well as cells that do not express HLA-A0201 (HEK293T) and MAGE-A genes (911 and HEK293T).

Another antibody, comprising Vh and Vl domains (scFv) with specificity for complexes of HLA-A01, presenting a MAGE-A1 peptide was also analyzed. The scFv-BTX construct was coupled to the HPMA polymer containing doxorubicin and incubated with MAGE-A1 positive and MAGE-A1 negative cells. Apoptosis is shown by staining for active caspase-3.

4.2: Detection of Active Caspase-3.

A classical intra-cellular hallmark for apoptosis is the presence of active caspase-3. To determine whether or not the antibodies of the disclosure induce active caspase-3, Daju, Mel624 and MDN cells are incubated with various concentrations of antibodies of the disclosure. After four and 13 hours FAM-DEVD-FMK, a fluorescently caspase-3/7 inhibitor, is added and positively stained cells are visualized by fluorescent microscopy and flow-cytometry. Caspase-3 activity is shown in antigen positive cells and not in antigen negative cells, with the (fragment of the) antigen providing the specific target-binding site for the antibodies of the disclosure.

4.3 Treatment of Tumor Bearing Mice with Immunoglobulins Provided with a Toxic Moiety.

Nude mice (NOD-scid, 8 per group) with a palpable subcutaneous transplantable human tumor (Daju or MDN) are injected with different doses of immunoglobulins provided with a toxic moiety. As a control mice are treated with standard chemotherapy or receive an injection with PBS. Mice receiving an optimal dose of the immunoglobulins provided with a toxic moiety survive significantly longer that those mice receiving chemotherapy or PBS, when the aberrant cells expose the target binding sites for the antibodies of the disclosure.

Example 5: Selection of Llama VHH with Specificity for HLA-A0201/FLWGPRALV and HLA-A02011 YLEYRQVPG Selection of Llama VHH fragments with specificity for HLA-A0201/FLWGPRALV [SEQ ID NO:23] (A2/FLW) and HLA-A0201/YLEYRQVPG [SEQ ID NO:3] (A2/YLE) were performed on CMT64 cells stably expressing these HLA/peptide complexes. Llama VHH phages ($10^{11}$ colony forming units) were first pre-incubated for one hour at room temperature in PBS containing 2% FCS (PBSF). In parallel, $1.0 \times 10^6$ CMT64-A2/FLW and $1.0 \times 10^6$ CMT64 A2/YLE cells were equilibrated for one hour in PBSF. To deplete for non-specific binding phages $10 \times 10^6$ CMT 64 cells expressing either A2/FLW or A2/YLE were incubated for one hour with the llama VHH. The non-bound fractions were then incubated (1 hr at 4° C.) with A2/FLW or A2/YLE expressing CMT64 cells. After extensive washing, bound phages were eluted by adding 500 μl freshly prepared tri-ethylamine (100 mM). The pH of the solution was neutralized by the addition of 500 μl 1 M Tris (pH 7.5). The eluted phages were incubated with logarithmic growing *E. Coli* TG1 cells ($OD_{600\,nm}$ of 0.5) for 30 minutes at 37° C. Bacteria were grown overnight on 2xTYAG plates. Next day, colonies were harvested. After four rounds of selection individual clones were selected and tested for specificity of binding.

5.2: Llama VHH Specific for HLA-A0201/Multi-MAGE-A Epitopes Bind Antigen Positive Cells.

To determine the cell-binding capacity of the A2/FLW and A2/YLE selected VHH soluble VHH fragments were made by induction of TG-1 bacteria. TG-1 containing pHen-VHH were grown until OD=0.8 and Fab production was induced by addition of 1 mM IPTG. After 13 hours induction, the bacterial periplasmic fraction was isolated and dialyzed overnight. Next day soluble VHH fragments were purified by IMAC.

CMT 64 cells (0.5×10⁶) expressing either HLA-A0210/YLEYRQVPG [SEQ ID NO:3], HLA-A0201/FLWGPRALV [SEQ ID NO:23], or CMT 64 cells that do not express human HLA were incubated with purified VHH fragments for one hour at 4° C. As shown in FIG. 7 the A2/FLW specific VHH bind HLA-A0201/FLWGPRALV [SEQ ID NO:23] expressing CMT64 cells and not CMT 64 cells that do not express human HLA or that do express the irrelevant HLA-A0201/YLEYRQVPG [SEQ ID NO:23] molecules. The A2/YLE specific VHH only bind HLA-A2/YLEYRQVPG [SEQ ID NO:23] expressing CMT64 cells and not A2/FLW positive CMT64 cells and CMT64 cells that do not express human HLA.

phages AH5, CB1, CG1, BD5 and BC7 and analyzed by flow-cytometry using anti-phage antibodies and a fluorescently labeled secondary antibody.

FIG. 3: Phages expressing HLA-A2/multi-MAGE-A specific Fab bind tumor cells of distinct histologic origin. Phages AH5, CB1 and CG1 specific for HLA-A0201/multi-MAGE-A and a positive control phage specific for HA-0101/MAGE-A1 were used for staining of distinct tumor cell lines. To this end the prostate cancer cell line LNCaP, the multiple myeloma cell line MDN, the melanoma cell lines MZ2-MEL43 and G43, and the breast cancer cell line MDA-MD157 were incubated with the different phages (30 minutes at 4° C.), bound phages were then detected by flow cytometry using anti-phage antibodies and fluorescently labeled secondary antibodies.

FIG. 4: Phage AH5 specifically binds HLA-A0201/multi-MAGE-A complexes only. To determine specificity of the phage AH5 an ELISA was performed using relevant and irrelevant peptide/MHC complexes. HLA-A0201 with

TABLE 1

Examples of the frequency of MAGE-A expression by human cancers.
Frequency of expression (%)

| Cancer | MAGE-A1 | MAGE-A2 | MAGE-A3 | MAGE-A4 | MAGE-A6 | MAGE-A10 | MAGE-A11 |
|---|---|---|---|---|---|---|---|
| Melanoma | 16 | E | 36 | E | 64 | E | 74 |
| Head and neck | 25 | 42 | 33 | 8 | N | N | N |
| Bladder | 21 | 30 | 35 | 33 | 15 | N | 9 |
| Breast | 6 | 19 | 10 | 13 | 5 | N | N |
| Colorectal | N | 5 | 5 | N | 5 | N | N |
| Lung | 21 | 30 | 46 | 11 | 8 | N | N |
| Gastric | 30 | 22 | 57 | N | N | N | N |
| Ovarian | 55 | 32 | 20 | E | 20 | N | N |
| Osteosarcoma | 62 | 75 | 62 | 12 | 62 | N | N |
| hepatocarcinoma | 68 | 30 | 68 | N | 30 | 30 | 30 |
| Renal cell carcinoma | 22 | 16 | 76 | 30 | N | N | N |

E, expressed but the frequency is not known; N, expression by tumors has never been observed

Panel A. Cartoon displaying the topology of the twelve immunoglobulin domains assembled in an immunoglobulin G. Panel B. Examples are provided of preferred immunoglobulins provided with a toxic moiety, according to the disclosure. Shown are immunoglobulins provided with a single toxic moiety such as, for example, a cytostatic agent, linked to the immunoglobulin with a chemical linker (exemplified by I. and II.; immunoglobulin-toxic moiety conjugates), or immunoglobulins provided with a single toxic moiety, linked to the immunoglobulin with a peptide linker (exemplified by III.; fused immunoglobulin-toxic moiety molecule). In IV., an immunoglobulin provided with a toxic moiety, according to the disclosure, is shown, comprising one immunoglobulin heavy chain comprising a fused proteinaceous toxic moiety, comprising immunoglobulin variable regions specific for a certain binding site, and comprising a second immunoglobulin heavy chain comprising immunoglobulin variable regions specific for a different binding site. Of course, also part of the disclosure are bi-specific immunoglobulins provided with a toxic moiety, according to the disclosure, comprising two heavy chains comprising different immunoglobulin variable regions specific for different binding sites and further comprising the same or different proteinaceous toxic moieties fused two the heavy chains. Of course, as part of the disclosure, more than one and typically two to six toxic moiety molecules can be fused or conjugated to an immunoglobulin molecule.

Figure 1:
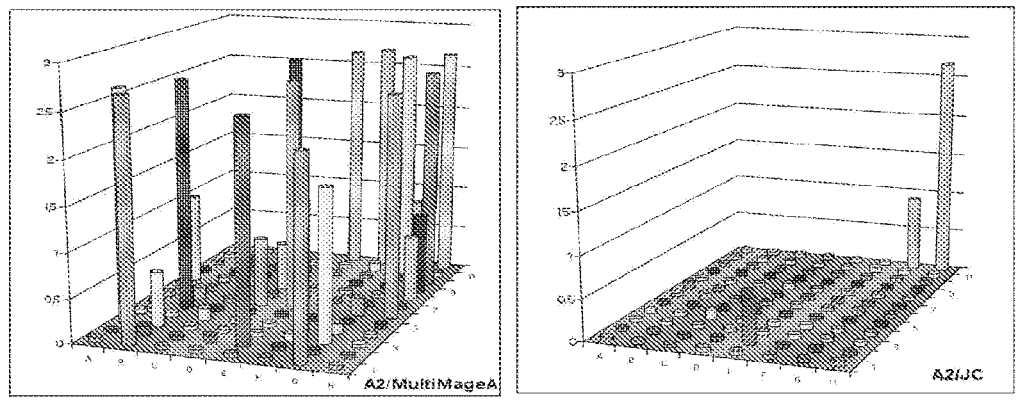
FIG. 1: Specific binding of HLA-A0201/multi-MAGE-A specific phage clones isolated from a large human non-immune antibody Fab phage library. Individual antibody Fab expressing phages that were selected against biotinylated HLA-A0201/multi-MAGE-A were analyzed by ELISA for their capacity to bind the relevant peptide/MHC complex only. Streptavidin coated 96 well plates were incubated with soluble HLA-A0201/multi-MAGE-A (A2/multiMage) or HLA-A0201/JCV (A2/JC) peptide/MHC complexes (10 μg/ml), washed to remove non-bound complexes and incubated with individual phage clones. Non-binding phages were first removed by three washes with PBS/Tween, followed by incubation with anti-M13 antibody (1 μg/ml, Amersham) for one hour by room temperature. Finally, the wells were incubated with an HRP-labeled secondary antibody and bound phages detected.
Figure 2:
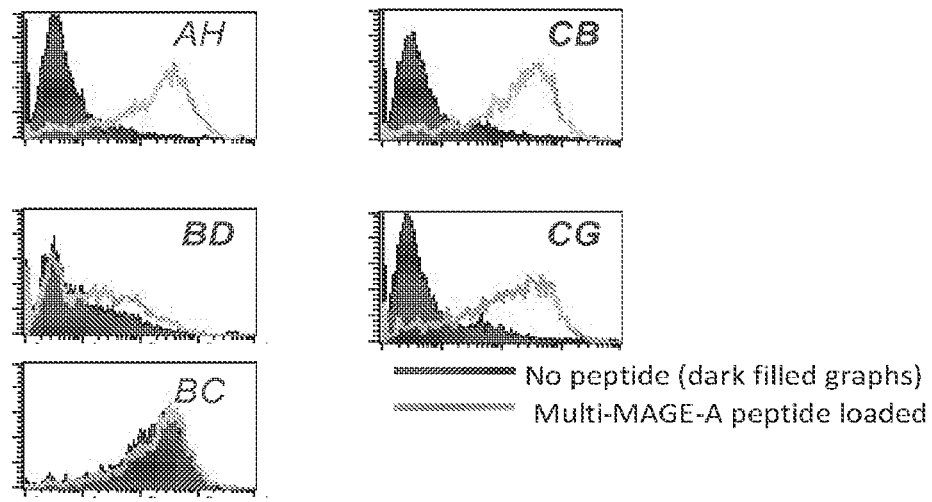
FIG. 2: Phages AH5, CB1 and CG1 specifically bind cells presenting the multi-MAGE-A peptide. Phages AH5, CB1, CG1, BD5 and BC7 that had shown specific binding in ELISA using the relevant HLA-A201/multi-MAGE-A complex and an irrelevant HLA-A201 complex loaded with a JCV peptide were analyzed for their capacity to bind cells presenting the multi-MAGE-A peptide in HLA-A0201 molecules. To this end, human B-LCL (BSM) were loaded with multi-MAGE-A peptide (10 μg in 100 μl PBS) for 30 minutes at 37° C., followed by incubation with the Fab multi-MAGE-A, gp100, JCV and MAGE-C2 peptides, as well as HLA-A1 with MAGE-A1 peptide were coated on streptavidin 96 well plates and incubated with phage AH5.
Figure 3:
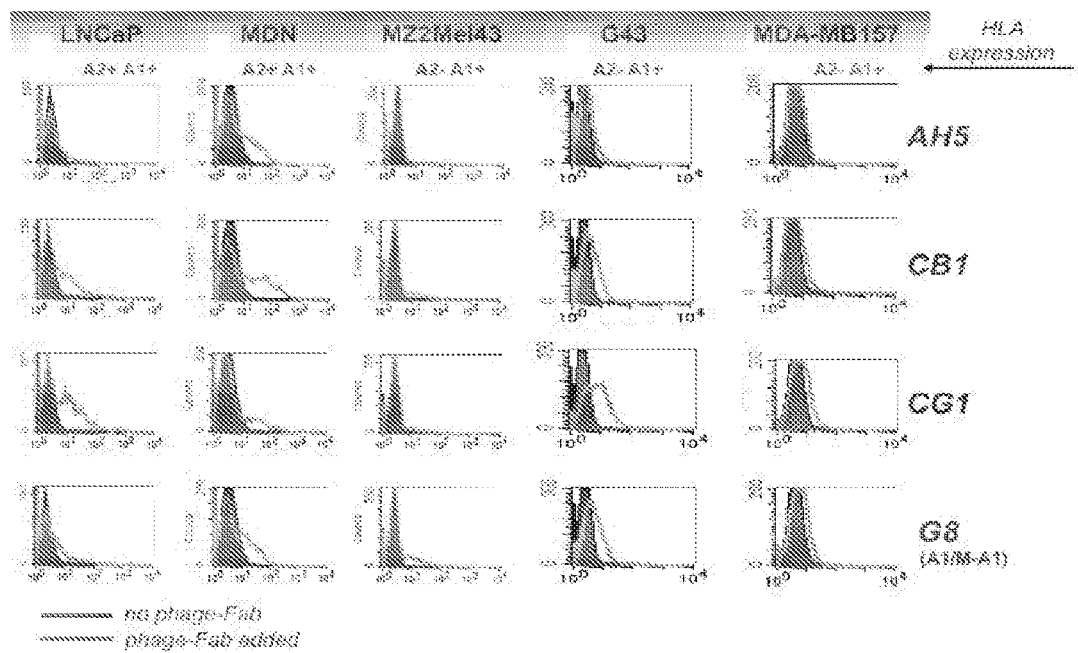
Figure 4:
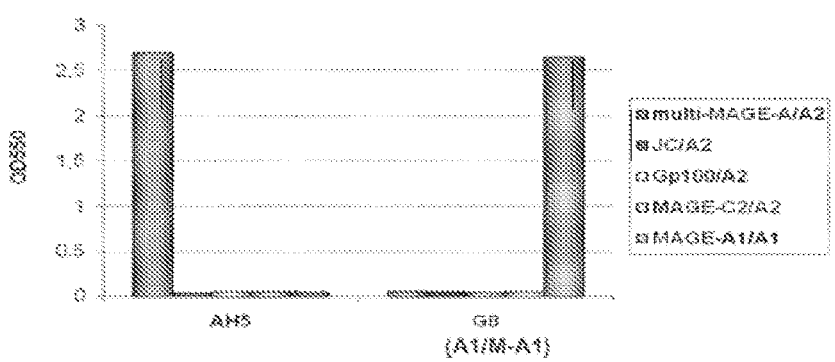
Figure 5:
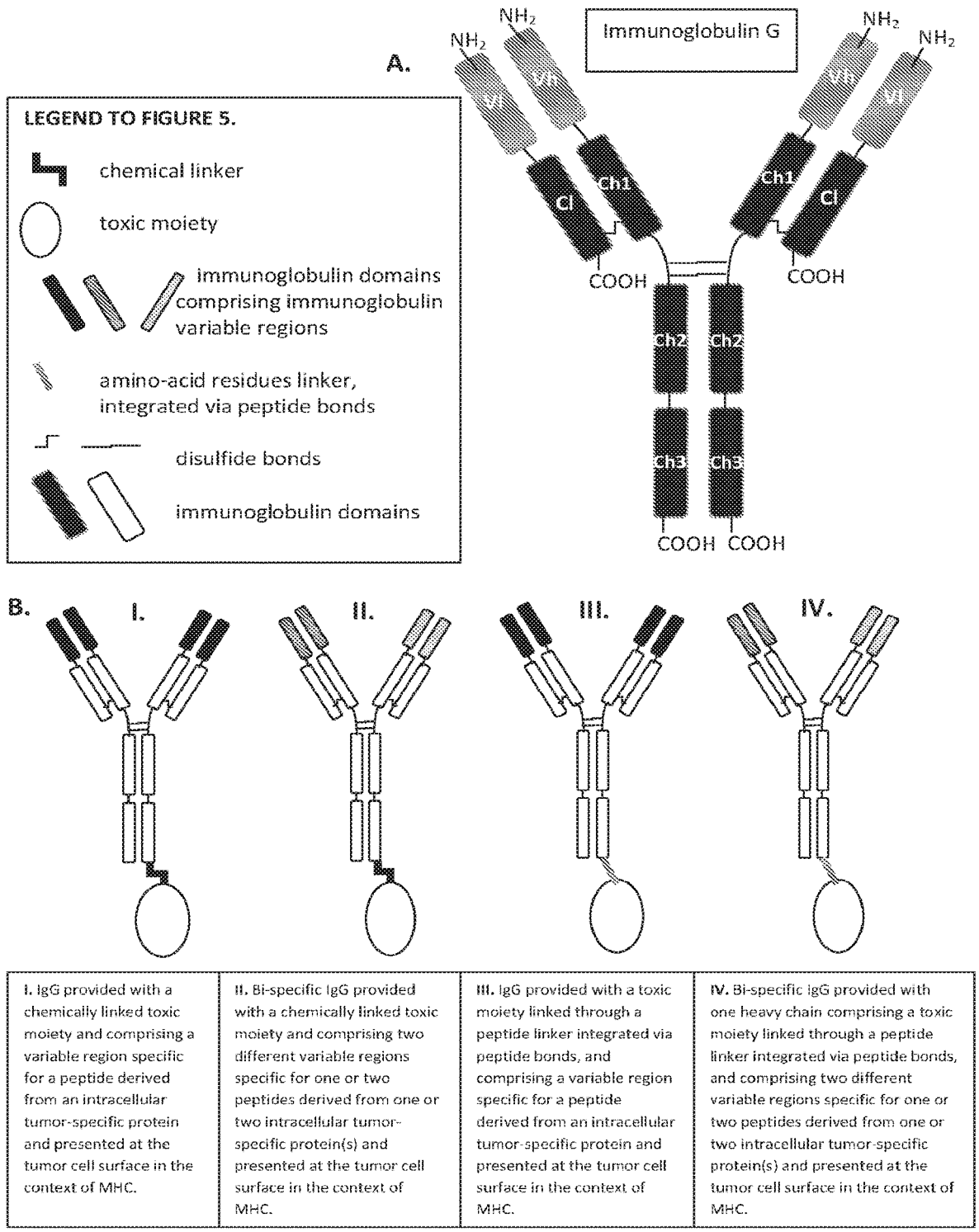
FIG. 5: Cartoon displaying examples of preferred immunoglobulins provided with a toxic moiety, according to the disclosure.
Figure 6:
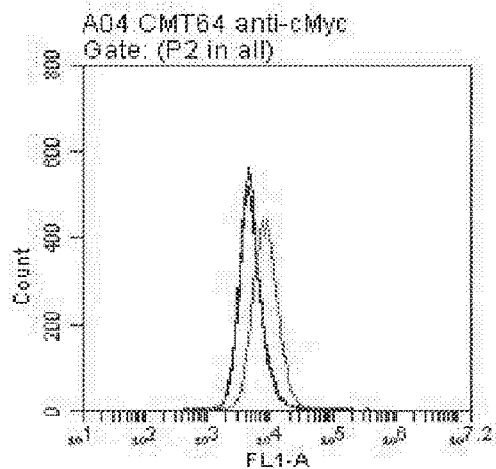

FIG. 6: Human Fab phage F9 specifically binds HLA-A2/FLWGPRALV positive CMT64 mouse lung tumor cells.

Human Fab clone F9 was analyzed for its capacity to bind mouse lung tumor cells (CMT64) stably expressing the HLA-A2/FLWGPRALV [SEQ ID NO:23] complex. Purified Clone F9 Fab fragments (3 µg total) were incubated with 0.5×10⁶ CMT64 cells that do not express human HLA, that express HLA-A2/YLEYRQVPG [SEQ ID NO:3] or that express HLA-A2/FLWGPRALV [SEQ ID NO:23]. After one hour incubation on ice CMT64 cells were incubated with a fluorescently labeled secondary antibody and analyzed by flow cytometry.

Figure 7:
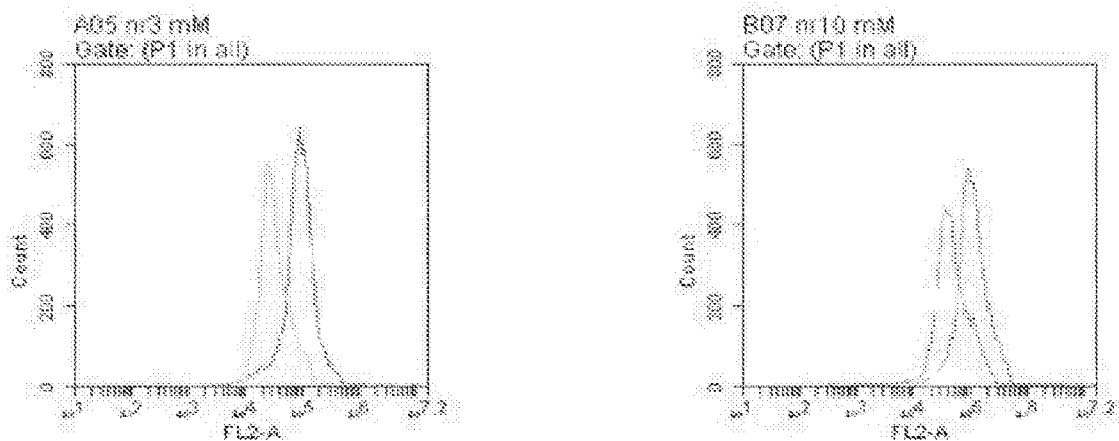

FIG. 7: Llama VHH specifically binds CMT64 mouse lung tumor cells expressing human HLA-A2/multi-MAGE-A.

Llama VHH specific for A2/FLW or A2/YLE were analyzed by flow cytometry for their binding capacity to CMT64 cells expressing these human HLA-A0201/multi-MAGE-A complexes. Purified VHH fragments (3 µg total) were incubated with 0.5×10⁶ CMT64 cells that do not express human HLA, that express HLA-A2/YLEYRQVPG [SEQ ID NO:3] or that express HLA-A2/FLWGPRALV [SEQ ID NO:23]. After one hour incubation on ice CMT64 cells were incubated with a fluorescently labeled secondary antibody and analyzed by flow cytometry.

FIG. 8: MAGE-A expression in human prostate cancer cell lines and prostate cancer xenografts.

```
                        SEQUENCE IDENTIFIERS

SEQ ID NO: 1. Amino acid sequence Vh AH5
QLQLQESGGG VVQPGRSLRL SCAASGFTFS SYGMHWVRQA PGKEREGVAV
ISYDGSNKYY ADSVKGRFTI SRDNSKNTLY LQMNSLRAED TAVYYCAGGS
YYVPDYWGQG TLVTVSSGST SGS SEQ ID NO: 3. Amino acid sequence MHC-1 HLA-A0201 presentable peptide in MAGE-A
YLEYRQVPG SEQ ID NO: 4. Amino acid sequence MHC-1 HLA-CW7 presentable peptide in MAGE-A
EGDCAPEEK SEQ ID NO: 5. Amino acid sequence MHC-1 HLA-A0201 presentable peptide in MAGE-A1
YLEYRQVPD SEQ ID NO: 6. Amino acid sequence MHC-1 HLA-A0201 presentable peptide in MAGE-A1
with enhanced binding capacity for HLA-A0201
YLEYRQVPV SEQ ID NO: 7. Amino acid sequence Vh binding domain 11H
EVQLVQSGGG LVKPGGSLRL SCAASGFTFS DYYMSWIRQA PGKGLEWLSY
ISSDGSTIYY ADSVKGRFTV SRDNAKNSLS LQMNSLRADD TAVYYCAVSP
RGYYYYGLDL WGQGTTVTVS S SEQ ID NO: 8, amino acid sequence of MAGE-A3 peptide epitope binding to HLA
IMPKAGLLI SEQ ID NO: 9, amino acid sequence of MAGE-A3 peptide epitope binding to HLA
KKLLTQHFVQENYLEY SEQ ID NO: 10, amino acid sequence of MAGE peptide epitope binding to HLA
EADPTGHSY SEQ ID NO: 11, amino acid sequence of MAGE peptide epitope binding to HLA
SLFRAVITK SEQ ID NO: 12, amino acid sequence of MAGE peptide epitope binding to HLA
NYKHCFPEI SEQ ID NO: 13, amino acid sequence of MAGE peptide epitope binding to HLA
EVYDGREHSA SEQ ID NO: 14, amino acid sequence of MAGE peptide epitope binding to HLA
REPVTKAEML SEQ ID NO: 15, amino acid sequence of MAGE peptide epitope binding to HLA
DPARYEFLW SEQ ID NO: 16, amino acid sequence of MAGE peptide epitope binding to HLA
SAFPTTINF SEQ ID NO: 17, amino acid sequence of MAGE peptide epitope binding to HLA
SAYGEPRKL SEQ ID NO: 18, amino acid sequence of MAGE peptide epitope binding to HLA
SAYGEPRKL SEQ ID NO: 19, amino acid sequence of MAGE peptide epitope binding to HLA
KMVELVHFL
```

SEQUENCE IDENTIFIERS

SEQ ID NO: 20, amino acid sequence of MAGE peptide epitope binding to HLA
YLQLVFGIEV SEQ ID NO: 21, amino acid sequence of MAGE peptide epitope binding to HLA
EYLQLVFGI SEQ ID NO: 22, amino acid sequence of MAGE peptide epitope binding to HLA
EADPIGHLY SEQ ID NO: 23, amino acid sequence of MAGE peptide epitope binding to HLA
FLWGPRALV SEQ ID NO: 24, amino acid sequence of MAGE peptide epitope binding to HLA
MEVDPIGHLY SEQ ID NO: 25, amino acid sequence of MAGE peptide epitope binding to HLA
WQYFFPVIF SEQ ID NO: 26, amino acid sequence of MAGE peptide epitope binding to HLA
GVYDGREHTV SEQ ID NO: 27, amino acid sequence of MAGE peptide epitope binding to HLA
MVKISGGPR SEQ ID NO: 28, amino acid sequence of MAGE peptide epitope binding to HLA
GLYDGMEHL SEQ ID NO: 29, amino acid sequence of MAGE peptide epitope binding to HLA
VRIGHLYIL SEQ ID NO: 30, amino acid sequence of BAGE peptide epitope binding to HLA
AARAVFLAL SEQ ID NO: 31, amino acid sequence of DAM-6 and DAM-10 peptide epitope binding to HLA
FLWGPRAYA SEQ ID NO: 32, amino acid sequence of GAGE-1/-2/-8 peptide epitope binding to HLA
YRPRPRRY SEQ ID NO: 33, amino acid sequence of GAGE-3/-4/-5/-6/-7B peptide epitope binding to HLA
YYWPRPRRY SEQ ID NO: 34, amino acid sequence of NA88-A peptide epitope binding to HLA
MTQGQHFLQKV SEQ ID NO: 35, amino acid sequence of NY-ESO-1 peptide epitope binding to HLA
SLLMWITQCFL SEQ ID NO: 36, amino acid sequence of NY-ESO-1a peptide epitope binding to HLA
SLLMWITQC SEQ ID NO: 37, amino acid sequence of NY-ESO-1a peptide epitope binding to HLA
QLSLLMWIT SEQ ID NO: 38, amino acid sequence of NY-ESO-1a peptide epitope binding to HLA
ASGPGGGAPR SEQ ID NO: 39, HPV 16 E6 T-cell epitope binding to HLA A1
FQDPQERPR SEQ ID NO: 40, HPV 16 E6 T-cell epitope binding to HLA A1
TTLEQQYNK SEQ ID NO: 41, HPV 16 E6 T-cell epitope binding to HLA A1
ISEYRHYCYS SEQ ID NO: 42, HPV 16 E6 T-cell epitope binding to HLA A1
GTTLEQQYNK SEQ ID NO: 43, HPV 16 E6 T-cell epitope binding to HLA A2
KISEYRHYC

SEQUENCE IDENTIFIERS

SEQ ID NO: 44, HPV 16 E6 T-cell epitope binding to HLA A2
YCYSIYGTTL

SEQ ID NO: 45, HPV 16 E6 T-cell epitope binding to HLA A3
LLRREVYDF

SEQ ID NO: 46, HPV 16 E6 T-cell epitope binding to HLA A3
IVYRDGNPY

SEQ ID NO: 47, HPV 16 E6 T-cell epitope binding to HLA A11
TTLEQQYNK

SEQ ID NO: 48, HPV 16 E6 T-cell epitope binding to HLA A24
CYSLYGTTL

SEQ ID NO: 49, HPV 16 E6 T-cell epitope binding to HLA A24
KLPQLCTEL

SEQ ID NO: 50, HPV 16 E6 T-cell epitope binding to HLA A24
HYCYSLYGT

SEQ ID NO: 51, HPV 16 E6 T-cell epitope binding to HLA A24
LYGTTLEQQY

SEQ ID NO: 52, HPV 16 E6 T-cell epitope binding to HLA A24
EVYDFAFRDL

SEQ ID NO: 53, HPV 16 E6 T-cell epitope binding to HLA A24
VYDFAFRDLC

SEQ ID NO: 54, HPV 16 E6 T-cell epitope binding to HLA A*0201
29-TIHDIILECV-38

SEQ ID NO: 55, HPV 16 E7 T-cell epitope binding to HLA A*0201
86-TLGIVCPI-93

SEQ ID NO: 56, HPV 16 E7 T-cell epitope binding to HLA A*0201
82-LLMGTLGIV-90

SEQ ID NO: 57, HPV 16 E7 T-cell epitope binding to HLA A*0201
85-GTLGIVCPI-93

SEQ ID NO: 58, HPV 16 E7 T-cell epitope binding to HLA A*0201
86-TLGIVCPIC-94

SEQ ID NO: 59, HPV E7 T-cell epitope binding to HLA DR
1-MHGDTPTLHEYD-12

SEQ ID NO: 60, HPV E7 T-cell epitope binding to HLA DR
48-DRAHYNIVTFCCKCD-62

SEQ ID NO: 61, HPV E7 T-cell epitope binding to HLA DR
62-DSTLRLCVQSTHVD-75

SEQ ID NO: 62, HPV E7 T-cell epitope binding to HLA A*201
7-TLHEYMLDL-15

SEQ ID NO: 63, HPV E7 T-cell epitope binding to HLA A*201
11-YMLDLQPETT-20

SEQ ID NO: 64, HPV E7 T-cell epitope binding to HLA A*201
11-YMLDLQPET-19

SEQ ID NO: 65, HPV E7 T-cell epitope binding to HLA A*201
12-MLDLQPETT-20

SEQ ID NO: 66, HPV E7 T-cell epitope binding to HLA B18
16-QPETTDLYCY-25

SEQ ID NO: 67, HPV E7 T-cell epitope binding to HLA B18
44-QAEPDRAHY-52

SEQ ID NO: 68, HPV E7 T-cell epitope binding to HLA B18
46-EPDRAHYNIV-55

SEQUENCE IDENTIFIERS

SEQ ID NO: 69, HPV E7 T-cell epitope binding to HLA DQ2
35-EDEIDGPAGQAEPDRA-50

SEQ ID NO: 70, HPV E7 T-cell epitope binding to HLA DR3
43-GQAEPDRAHYNIVTFCCKCDSTLRLCVQSTHVDIR-77

SEQ ID NO: 71, HPV E7 T-cell epitope binding to HLA DR15
50-AHYNIVTFCCKCD-62

SEQ ID NO: 72, HPV E7 T-cell epitope binding to HLA DR17
58-CCKCDSTLRLC-68

SEQ ID NO: 73, HPV E7 T-cell epitope binding to HLA-DRB1*0901
61-CDSTLRLCVQSTHVDIRTLE-80

SEQ ID NO: 74, PSA T-cell epitope binding to HLA-A2
146-KLQCVDLHV-154

SEQ ID NO: 75, PSA T-cell epitope binding to HLA-A2
141-FLTPKKLQCV-150

SEQ ID NO: 76, PSA T-cell epitope binding to HLA-A2
154-VISNDVCAQV-163

SEQ ID NO: 77, PSA T-cell epitope binding to HLA-A2
154-YISNDVCAQV-163

SEQ ID NO: 78, PSA T-cell epitope binding to HLA-A3
162-QVHPQKVTK-170

SEQ ID NO: 79, PSA T-cell epitope binding to HLA-A24
152-CYASGWGSI-160

SEQ ID NO: 80, PSA T-cell epitope binding to HLA-A24
248-HYRKWIKDTI-257

SEQ ID NO: 81, PSMA T-cell epitope binding to HLA-A2
4-LLHETDSAV-12

SEQ ID NO: 82, PSMA T-cell epitope binding to HLA-A2
711-ALFDIESKV-719

SEQ ID NO: 83, PSMA T-cell epitope binding to HLA-A2
27-VLAGGFFLL-35

SEQ ID NO: 84, PSMA T-cell epitope binding to HLA-A24
178-NYARTEDFF-186

SEQ ID NO: 85, PSMA T-cell epitope binding to HLA-A24
227-LYSDPADYF-235

SEQ ID NO: 86, PSMA T-cell epitope binding to HLA-A24
624-TYSVSFDSL-632

SEQ ID NO: 87, PAP T-cell epitope binding to HLA-A2
299-ALDVYNGLL-307

SEQ ID NO: 88, PAP T-cell epitope binding to HLA-A24
213-LYCESVHNF-221

SEQ ID NO: 89, PAP T-cell epitope binding to MHC-2
199-GQDLFGIWSKVYDPL-213

SEQ ID NO: 90, PAP T-cell epitope binding to MHC-2
228-TEDTMTKLRELSELS-242

SEQ ID NO: 91, PSCA T-cell epitope binding to HLA-A2
14-ALQPGTALL-22

SEQ ID NO: 92, PSCA T-cell epitope binding to HLA-A2
105-AILALLPAL-113

SEQ ID NO: 93, PSCA T-cell epitope binding to HLA-A2
7-ALLMAGLAL-15

-continued

SEQUENCE IDENTIFIERS

SEQ ID NO: 94, PSCA T-cell epitope binding to HLA-A2
21-LLCYSCKAQV-30

SEQ ID NO: 95, Kallikrein 4 T-cell epitope binding to DRB1*0404
155-LLANGRMPTVLQCVN-169

SEQ ID NO: 96, Kallikrein 4 T-cell epitope binding to DRB1*0701
160-RMPTVLQCVNVSVVS-174

SEQ ID NO: 97, Kallikrein 4 T-cell epitope binding to DPB1*0401
125-SVSESDTIRSISIAS-139

SEQ ID NO: 98, EBV nuclear antigen 3 T-cell epitope binding to MHC 1 HLA B8
FLRGRAYGL SEQ ID NO: 99, HLA-A2 restricted CD8+ T-cell epitope of PAP binding to HLA-A2
FLFLLFFWL SEQ ID NO: 100, HLA-A2 restricted CD8+ T-cell epitope of PAP binding to HLA-A2
TLMSAMTNL SEQ ID NO: 101, HLA-A2 restricted CD8+ T-cell epitope of PAP binding to HLA-A2
ALDVYNGLL SEQ ID NO: 102, human HLA-A2.1-restricted CTL epitope of PAP-3 binding to HLA
A2.1
ILLWQPIPV SEQ ID NO: 103, HLA-A2.1-restricted CTL epitope of STEAP-3 binding to HLA-A2.1
LLLGTIHAL SEQ ID NO: 104, HLA-A2.1-restricted CTL epitope of MUC-1 and MUC-2 binding to
HLA-A2.1
CHGVTSAPDTRPAPGSTAPPAHGVTSAPDTRPA SEQ ID NO: 105, single chain HLA-A0201/FLWGPRALV construct.
MAVMAPRTLVLLLSGALALTQTWAFLWGPRALVGGGGSGGGGSGGGGSGGGGSGIQRTPKIQVYSRHP
AENGKSNFLNCYVSGFHPSDIEVDLLKNGERIEKVEHSDLSFSKDWSFYLLYYTEFTPTEKDEYACRVNH
VTLSQPKIVKWDRDMGGGGSGGGGSGGGGSGSHSMRYFFTSVSRPGRGEPRFIAVGYVDDTQFVRFDSDA
ASQRMEPRAPWIEQEGPEYWDGETRKVKAHSQTHRVDLGTLRGYYNQSESHTVQRMYGCDVGSDWRFLRG
YHQYAYDGKDYIALKEDLRSWTAADMAAQTTKHKWEAAHVAEQLRAYLEGTCVEWLRRYLENGKETLQRT
DSPKAHVTHHPRSKGEVTLRCWALGFYPADITLTWQLNGEELTQDMELVETRPAGDGTFQKWASVVVPLG
KEQNYTCRVYHEGLPEPLTLRWEPPPSTDSYMVIVAVLGVLGAMAIIGAVVAFVMKRRRNTGGGDYALAP
GSQSSEMSLRDCKA

REFERENCES

1. Stephanie Graff-Dubois, Olivier Faure, David-Alexandre Gross, Pedro Alves, Antonio Scardino, Salem Chouaib, Francois A. Lemonnier and Kostas Kosmatopoulos. Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy. *The Journal of Immunology,* 2002, 169: 575-580.
2. Hans J. de Haard, Nicole van Neer, Anneke Reurs, Simon E. Hufton, Rob C. Roovers, Paula Henderikx, Adriaan P. de Brume, Jan-Willem Arends, and Hennie R. Hoogenboom. A Large Non-immunized Human Fab Fragment Phage Library That Permits Rapid Isolation and Kinetic Analysis of High Affinity Antibodies. *The Journal of Biological Chemistry.* 1999, 274: 18218-18230.
3. Chames P, Hoogenboom H. R, Henderikx P. Selection of antigens against biotinylated antigens. In Antibody phage display, methods and protocols, Edited by P. M. O'Brien and R. Aitken. *Methods in Molecular Biology* 2002, 178:147-159.
4. Patrick Chames, Simon E. Hufton, Pierre G. Coulie, Barbara Uchanska-Ziegler, Hennie R. Hoogenboom. Direct selection of a human antibody fragment directed against the tumor T-cell epitope HLA-A1-MAGE-A1 from a nonimmunized phage-Fab library. *PNAS,* 2000. 97: 7969-7974.
5. H. M. Noteborn, Proteins selectively killing tumor cells. *Eur. J. Pharmacol.,* 2009. 625: 165-173.
6. Teicher, B. A. & Chari, R. V. J., Antibody conjugate therapeutics: challenges and potential. *Clin. Cancer Res.,* 2011, 17(20):6389-97.
7. McCurdy D K, Tai L Q, Imfeld K L, Schwartz M, Zaldivar F, Berman M A, Expression of melanoma antigen gene by cells from inflamed joints in juvenile rheumatoid arthritis, *J. Rheumatol.* 2002, 29:2219-2224.
8. Marcar L, Maclaine N J, Hupp T R, Meek D W, Mage-A cancer/testis antigens inhibit p53 function by blocking its interaction with chromatin, *Cancer Res.* 2010, 70:10362-10370.
9. Van den Eynde B. J., van der Bruggen P., T cell-defined tumor antigens. *Curr. Opin. Immunol.* 1997; 9: 684-93.
10. Houghton A. N., Gold J. S., Blachere N. E., Immunity against cancer: lessons learned from melanoma. *Curr. Opin. Mumma* 2001; 13: 134-40.

11. van der Bruggen P., Zhang Y., Chaux P., Stroobant V., Panichelli C., Schultz E. S., Chapiro J., Van den Eynde B. J., Brasseur F., Boon T., Tumor-specific shared antigenic peptides recognized by human T cells. *Immunol. Rev.* 2002; 188: 51-64.
12. Parmiani G., De Filippo A., Novellino L., Castelli C., Unique human tumor antigens: immunobiology and use in clinical trials. *J. Immunol.* 2007; 178: 1975-9.
13. Renkvist, N., Castelli, C., Robbins, P. F., Parmiani, G., A listing of human tumor antigens recognized by T-cells, *Cancer Immunol. Immunother.* 2001; 50: 3-15.
14. Ridgway, J. B. B., Presta, L. G., Carter, P., 'Knobs-into-holes' engineering of antibody CH3 domains for heavy chain heterodimerization *Protein Engineering*, 1996; 9, no. 7: 617-621.

The invention claimed is:

1. An immunoglobulin conjugated to a toxic moiety comprising at least an immunoglobulin region that specifically binds to an MHC-I-MAGE peptide complex,
   wherein the immunoglobulin region comprises a Vh domain comprising SEQ ID NO: 1;
   wherein the MAGE peptide of the MHC-I-MAGE peptide complex is derived from intracellular MAGE associated with aberrant cells; and
   wherein the MAGE peptide is a multi-MAGE epitope.

2. The immunoglobulin conjugated to a toxic moiety according to claim 1, wherein the immunoglobulin region further comprises a Vl.

3. The immunoglobulin conjugated to a toxic moiety of claim 1, wherein the MHC-I-MAGE peptide complex is specific for aberrant cells.

4. A pharmaceutical composition comprising:
   the immunoglobulin conjugated to a toxic moiety of claim 1, and suitable diluents and/or excipients.

5. A method of treating a host suffering from a disease associated with aberrant cells, the method comprising:
   administering the immunoglobulin conjugated to a toxic moiety of claim 1 to the host, for the treatment of the host suffering from a disease associated with aberrant cells.

6. The method according to claim 5, wherein the toxic moiety is internalized into an aberrant cell of the host.

7. A method of treating a subject determined to be suffering from cancer, the method comprising:
   administering the immunoglobulin conjugated to a toxic moiety of claim 1 to the host to treat cancer.

8. The method according to claim 7, wherein at least the toxic moiety is internalized into an aberrant cell of the subject.

9. The immunoglobulin conjugated to a toxic moiety of claim 3, wherein the MAGE is MAGE-A.

10. The immunoglobulin conjugated to a toxic moiety of claim 1, wherein the toxic moiety is a fusion protein fused to the immunoglobulin at the DNA level through a linking sequence.

11. The immunoglobulin conjugated to a toxic moiety of claim 1, wherein the MHC-I-MAGE peptide complex is upregulated on aberrant cells.

* * * * *

SEQUENCE LISTING

```
<160> NUMBER OF SEQ ID NOS: 112

<210> SEQ ID NO 1
<211> LENGTH: 123
<212> TYPE: PRT
<213> ORGANISM: Artificial
<220> FEATURE:
<223> OTHER INFORMATION: peptide3

<400> SEQUENCE: 1

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Arg Glu Gly Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Ser Tyr Tyr Val Pro Asp Tyr Trp Gly Gln Gly Thr Leu
            100                 105                 110

Val Thr Val Ser Ser Gly Ser Thr Ser Gly Ser
        115                 120

<210> SEQ ID NO 2

<400> SEQUENCE: 2

000

<210> SEQ ID NO 3
<211> LENGTH: 9
<212> TYPE: PRT
<213> ORGANISM: Artificial
<220> FEATURE:
<223> OTHER INFORMATION: peptide

<400> SEQUENCE: 3

Tyr Leu Glu Tyr Arg Gln Val Pro Gly
1               5

<210> SEQ ID NO 4
<211> LENGTH: 9
<212> TYPE: PRT
<213> ORGANISM: Artificial
<220> FEATURE:
<223> OTHER INFORMATION: peptide

<400> SEQUENCE: 4

Glu Gly Asp Cys Ala Pro Glu Glu Lys
1               5
```

<210> SEQ ID NO 5
<211> LENGTH: 9
<212> TYPE: PRT
<213> ORGANISM: Artificial
<220> FEATURE:
<223> OTHER INFORMATION: peptide

<400> SEQUENCE: 5

Tyr Leu Glu Tyr Arg Gln Val Pro Asp
1               5

<210> SEQ ID NO 6
<211> LENGTH: 9
<212> TYPE: PRT
<213> ORGANISM: Artificial
<220> FEATURE:
<223> OTHER INFORMATION: peptide

<400> SEQUENCE: 6

Tyr Leu Glu Tyr Arg Gln Val Pro Val
1               5

<210> SEQ ID NO 7
<211> LENGTH: 121
<212> TYPE: PRT
<213> ORGANISM: Artificial
<220> FEATURE:
<223> OTHER INFORMATION: peptide

<400> SEQUENCE: 7

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Ser Asp Gly Ser Thr Ile Tyr Tyr Ala Asp Ser Val
    50                  55                  60

Lys Gly Arg Phe Thr Val Ser Arg Asp Asn Ala Lys Asn Ser Leu Ser
65                  70                  75                  80

Leu Gln Met Asn Ser Leu Arg Ala Asp Asp Thr Ala Val Tyr Tyr Cys
                85                  90                  95

Ala Val Ser Pro Arg Gly Tyr Tyr Tyr Gly Leu Asp Leu Trp Gly
            100                 105                 110

Gln Gly Thr Thr Val Thr Val Ser Ser
        115                 120

<210> SEQ ID NO 8
<211> LENGTH: 9
<212> TYPE: PRT
<213> ORGANISM: Artificial
<220> FEATURE:
<223> OTHER INFORMATION: peptide

<400> SEQUENCE: 8

Ile Met Pro Lys Ala Gly Leu Leu Ile
1               5

<210> SEQ ID NO 9
<211> LENGTH: 16
<212> TYPE: PRT
<213> ORGANISM: Artificial

```
<220> FEATURE:
<223> OTHER INFORMATION: peptide

<400> SEQUENCE: 9

Lys Lys Leu Leu Thr Gln His Phe Val Gln Glu Asn Tyr Leu Glu Tyr
1               5                   10                  15

<210> SEQ ID NO 10
<211> LENGTH: 9
<212> TYPE: PRT
<213> ORGANISM: Artificial
<220> FEATURE:
<223> OTHER INFORMATION: peptide

<400> SEQUENCE: 10

Glu Ala Asp Pro Thr Gly His Ser Tyr
1               5

<210> SEQ ID NO 11
<211> LENGTH: 9
<212> TYPE: PRT
<213> ORGANISM: Artificial
<220> FEATURE:
<223> OTHER INFORMATION: peptide

<400> SEQUENCE: 11

Ser Leu Phe Arg Ala Val Ile Thr Lys
1               5

<210> SEQ ID NO 12
<211> LENGTH: 9
<212> TYPE: PRT
<213> ORGANISM: Artificial
<220> FEATURE:
<223> OTHER INFORMATION: peptide

<400> SEQUENCE: 12

Asn Tyr Lys His Cys Phe Pro Glu Ile
1               5

<210> SEQ ID NO 13
<211> LENGTH: 10
<212> TYPE: PRT
<213> ORGANISM: Artificial
<220> FEATURE:
<223> OTHER INFORMATION: peptide

<400> SEQUENCE: 13

Glu Val Tyr Asp Gly Arg Glu His Ser Ala
1               5                   10

<210> SEQ ID NO 14
<211> LENGTH: 10
<212> TYPE: PRT
<213> ORGANISM: Artificial
<220> FEATURE:
<223> OTHER INFORMATION: peptide

<400> SEQUENCE: 14

Arg Glu Pro Val Thr Lys Ala Glu Met Leu
1               5                   10

<210> SEQ ID NO 15
<211> LENGTH: 9
<212> TYPE: PRT
<213> ORGANISM: Artificial
<220> FEATURE:
```

```
<223> OTHER INFORMATION: peptide

<400> SEQUENCE: 15

Asp Pro Ala Arg Tyr Glu Phe Leu Trp
1               5

<210> SEQ ID NO 16
<211> LENGTH: 9
<212> TYPE: PRT
<213> ORGANISM: Artificial
<220> FEATURE:
<223> OTHER INFORMATION: peptide

<400> SEQUENCE: 16

Ser Ala Phe Pro Thr Thr Ile Asn Phe
1               5

<210> SEQ ID NO 17
<211> LENGTH: 9
<212> TYPE: PRT
<213> ORGANISM: Artificial
<220> FEATURE:
<223> OTHER INFORMATION: peptide

<400> SEQUENCE: 17

Ser Ala Tyr Gly Glu Pro Arg Lys Leu
1               5

<210> SEQ ID NO 18
<211> LENGTH: 9
<212> TYPE: PRT
<213> ORGANISM: Artificial
<220> FEATURE:
<223> OTHER INFORMATION: peptide

<400> SEQUENCE: 18

Ser Ala Tyr Gly Glu Pro Arg Lys Leu
1               5

<210> SEQ ID NO 19
<211> LENGTH: 9
<212> TYPE: PRT
<213> ORGANISM: Artificial
<220> FEATURE:
<223> OTHER INFORMATION: peptide

<400> SEQUENCE: 19

Lys Met Val Glu Leu Val His Phe Leu
1               5

<210> SEQ ID NO 20
<211> LENGTH: 10
<212> TYPE: PRT
<213> ORGANISM: Artificial
<220> FEATURE:
<223> OTHER INFORMATION: peptide

<400> SEQUENCE: 20

Tyr Leu Gln Leu Val Phe Gly Ile Glu Val
1               5                   10

<210> SEQ ID NO 21
<211> LENGTH: 9
<212> TYPE: PRT
<213> ORGANISM: Artificial
<220> FEATURE:
<223> OTHER INFORMATION: peptide
```

```
<400> SEQUENCE: 21

Glu Tyr Leu Gln Leu Val Phe Gly Ile
1               5

<210> SEQ ID NO 22
<211> LENGTH: 9
<212> TYPE: PRT
<213> ORGANISM: Artificial
<220> FEATURE:
<223> OTHER INFORMATION: peptide

<400> SEQUENCE: 22

Glu Ala Asp Pro Ile Gly His Leu Tyr
1               5

<210> SEQ ID NO 23
<211> LENGTH: 9
<212> TYPE: PRT
<213> ORGANISM: Artificial
<220> FEATURE:
<223> OTHER INFORMATION: peptide

<400> SEQUENCE: 23

Phe Leu Trp Gly Pro Arg Ala Leu Val
1               5

<210> SEQ ID NO 24
<211> LENGTH: 10
<212> TYPE: PRT
<213> ORGANISM: Artificial
<220> FEATURE:
<223> OTHER INFORMATION: peptide

<400> SEQUENCE: 24

Met Glu Val Asp Pro Ile Gly His Leu Tyr
1               5                   10

<210> SEQ ID NO 25
<211> LENGTH: 9
<212> TYPE: PRT
<213> ORGANISM: Artificial
<220> FEATURE:
<223> OTHER INFORMATION: peptide

<400> SEQUENCE: 25

Trp Gln Tyr Phe Phe Pro Val Ile Phe
1               5

<210> SEQ ID NO 26
<211> LENGTH: 10
<212> TYPE: PRT
<213> ORGANISM: Artificial
<220> FEATURE:
<223> OTHER INFORMATION: peptide

<400> SEQUENCE: 26

Gly Val Tyr Asp Gly Arg Glu His Thr Val
1               5                   10

<210> SEQ ID NO 27
<211> LENGTH: 9
<212> TYPE: PRT
<213> ORGANISM: Artificial
<220> FEATURE:
<223> OTHER INFORMATION: peptide
```

```
<400> SEQUENCE: 27

Met Val Lys Ile Ser Gly Gly Pro Arg
1               5

<210> SEQ ID NO 28
<211> LENGTH: 9
<212> TYPE: PRT
<213> ORGANISM: Artificial
<220> FEATURE:
<223> OTHER INFORMATION: peptide

<400> SEQUENCE: 28

Gly Leu Tyr Asp Gly Met Glu His Leu
1               5

<210> SEQ ID NO 29
<211> LENGTH: 9
<212> TYPE: PRT
<213> ORGANISM: Artificial
<220> FEATURE:
<223> OTHER INFORMATION: peptide

<400> SEQUENCE: 29

Val Arg Ile Gly His Leu Tyr Ile Leu
1               5

<210> SEQ ID NO 30
<211> LENGTH: 9
<212> TYPE: PRT
<213> ORGANISM: Artificial
<220> FEATURE:
<223> OTHER INFORMATION: peptide

<400> SEQUENCE: 30

Ala Ala Arg Ala Val Phe Leu Ala Leu
1               5

<210> SEQ ID NO 31
<211> LENGTH: 9
<212> TYPE: PRT
<213> ORGANISM: Artificial
<220> FEATURE:
<223> OTHER INFORMATION: peptide

<400> SEQUENCE: 31

Phe Leu Trp Gly Pro Arg Ala Tyr Ala
1               5

<210> SEQ ID NO 32
<211> LENGTH: 8
<212> TYPE: PRT
<213> ORGANISM: Artificial
<220> FEATURE:
<223> OTHER INFORMATION: peptide

<400> SEQUENCE: 32

Tyr Arg Pro Arg Pro Arg Arg Tyr
1               5

<210> SEQ ID NO 33
<211> LENGTH: 9
<212> TYPE: PRT
<213> ORGANISM: Artificial
<220> FEATURE:
<223> OTHER INFORMATION: peptide

<400> SEQUENCE: 33
```

Tyr Tyr Trp Pro Arg Pro Arg Arg Tyr
1               5

<210> SEQ ID NO 34
<211> LENGTH: 11
<212> TYPE: PRT
<213> ORGANISM: Artificial
<220> FEATURE:
<223> OTHER INFORMATION: peptide

<400> SEQUENCE: 34

Met Thr Gln Gly Gln His Phe Leu Gln Lys Val
1               5                   10

<210> SEQ ID NO 35
<211> LENGTH: 11
<212> TYPE: PRT
<213> ORGANISM: Artificial
<220> FEATURE:
<223> OTHER INFORMATION: peptide

<400> SEQUENCE: 35

Ser Leu Leu Met Trp Ile Thr Gln Cys Phe Leu
1               5                   10

<210> SEQ ID NO 36
<211> LENGTH: 9
<212> TYPE: PRT
<213> ORGANISM: Artificial
<220> FEATURE:
<223> OTHER INFORMATION: peptide

<400> SEQUENCE: 36

Ser Leu Leu Met Trp Ile Thr Gln Cys
1               5

<210> SEQ ID NO 37
<211> LENGTH: 9
<212> TYPE: PRT
<213> ORGANISM: Artificial
<220> FEATURE:
<223> OTHER INFORMATION: peptide

<400> SEQUENCE: 37

Gln Leu Ser Leu Leu Met Trp Ile Thr
1               5

<210> SEQ ID NO 38
<211> LENGTH: 10
<212> TYPE: PRT
<213> ORGANISM: Artificial
<220> FEATURE:
<223> OTHER INFORMATION: peptide

<400> SEQUENCE: 38

Ala Ser Gly Pro Gly Gly Gly Ala Pro Arg
1               5                   10

<210> SEQ ID NO 39
<211> LENGTH: 9
<212> TYPE: PRT
<213> ORGANISM: Artificial
<220> FEATURE:
<223> OTHER INFORMATION: peptide

<400> SEQUENCE: 39

Phe Gln Asp Pro Gln Glu Arg Pro Arg
1               5

<210> SEQ ID NO 40
<211> LENGTH: 9
<212> TYPE: PRT
<213> ORGANISM: Artificial
<220> FEATURE:
<223> OTHER INFORMATION: peptide

<400> SEQUENCE: 40

Thr Thr Leu Glu Gln Gln Tyr Asn Lys
1               5

<210> SEQ ID NO 41
<211> LENGTH: 10
<212> TYPE: PRT
<213> ORGANISM: Artificial
<220> FEATURE:
<223> OTHER INFORMATION: peptide

<400> SEQUENCE: 41

Ile Ser Glu Tyr Arg His Tyr Cys Tyr Ser
1               5                   10

<210> SEQ ID NO 42
<211> LENGTH: 10
<212> TYPE: PRT
<213> ORGANISM: Artificial
<220> FEATURE:
<223> OTHER INFORMATION: peptide

<400> SEQUENCE: 42

Gly Thr Thr Leu Glu Gln Gln Tyr Asn Lys
1               5                   10

<210> SEQ ID NO 43
<211> LENGTH: 9
<212> TYPE: PRT
<213> ORGANISM: Artificial
<220> FEATURE:
<223> OTHER INFORMATION: peptide

<400> SEQUENCE: 43

Lys Ile Ser Glu Tyr Arg His Tyr Cys
1               5

<210> SEQ ID NO 44
<211> LENGTH: 10
<212> TYPE: PRT
<213> ORGANISM: Artificial
<220> FEATURE:
<223> OTHER INFORMATION: peptide

<400> SEQUENCE: 44

Tyr Cys Tyr Ser Ile Tyr Gly Thr Thr Leu
1               5                   10

<210> SEQ ID NO 45
<211> LENGTH: 9
<212> TYPE: PRT
<213> ORGANISM: Artificial
<220> FEATURE:
<223> OTHER INFORMATION: peptide

<400> SEQUENCE: 45

Leu Leu Arg Arg Glu Val Tyr Asp Phe

```
<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Ile Val Tyr Arg Asp Gly Asn Pro Tyr
1               5

<210> SEQ ID NO 47
<211> LENGTH: 9
<212> TYPE: PRT
<213> ORGANISM: Artificial
<220> FEATURE:
<223> OTHER INFORMATION: peptide

<400> SEQUENCE: 47

Thr Thr Leu Glu Gln Gln Tyr Asn Lys
1               5

<210> SEQ ID NO 48
<211> LENGTH: 9
<212> TYPE: PRT
<213> ORGANISM: Artificial
<220> FEATURE:
<223> OTHER INFORMATION: peptide

<400> SEQUENCE: 48

Cys Tyr Ser Leu Tyr Gly Thr Thr Leu
1               5

<210> SEQ ID NO 49
<211> LENGTH: 9
<212> TYPE: PRT
<213> ORGANISM: Artificial
<220> FEATURE:
<223> OTHER INFORMATION: peptide

<400> SEQUENCE: 49

Lys Leu Pro Gln Leu Cys Thr Glu Leu
1               5

<210> SEQ ID NO 50
<211> LENGTH: 9
<212> TYPE: PRT
<213> ORGANISM: Artificial
<220> FEATURE:
<223> OTHER INFORMATION: peptide

<400> SEQUENCE: 50

His Tyr Cys Tyr Ser Leu Tyr Gly Thr
1               5

<210> SEQ ID NO 51
<211> LENGTH: 10
<212> TYPE: PRT
<213> ORGANISM: Artificial
<220> FEATURE:
<223> OTHER INFORMATION: peptide

<400> SEQUENCE: 51

Leu Tyr Gly Thr Thr Leu Glu Gln Gln Tyr
1               5                   10
```

<210> SEQ ID NO 52
<211> LENGTH: 10
<212> TYPE: PRT
<213> ORGANISM: Artificial
<220> FEATURE:
<223> OTHER INFORMATION: peptide

<400> SEQUENCE: 52

Glu Val Tyr Asp Phe Ala Phe Arg Asp Leu
1               5                   10

<210> SEQ ID NO 53
<211> LENGTH: 10
<212> TYPE: PRT
<213> ORGANISM: Artificial
<220> FEATURE:
<223> OTHER INFORMATION: peptide

<400> SEQUENCE: 53

Val Tyr Asp Phe Ala Phe Arg Asp Leu Cys
1               5                   10

<210> SEQ ID NO 54
<211> LENGTH: 10
<212> TYPE: PRT
<213> ORGANISM: Artificial
<220> FEATURE:
<223> OTHER INFORMATION: peptide

<400> SEQUENCE: 54

Thr Ile His Asp Ile Ile Leu Glu Cys Val
1               5                   10

<210> SEQ ID NO 55
<211> LENGTH: 8
<212> TYPE: PRT
<213> ORGANISM: Artificial
<220> FEATURE:
<223> OTHER INFORMATION: peptide

<400> SEQUENCE: 55

Thr Leu Gly Ile Val Cys Pro Ile
1               5

<210> SEQ ID NO 56
<211> LENGTH: 9
<212> TYPE: PRT
<213> ORGANISM: Artificial
<220> FEATURE:
<223> OTHER INFORMATION: peptide

<400> SEQUENCE: 56

Leu Leu Met Gly Thr Leu Gly Ile Val
1               5

<210> SEQ ID NO 57
<211> LENGTH: 9
<212> TYPE: PRT
<213> ORGANISM: Artificial
<220> FEATURE:
<223> OTHER INFORMATION: peptide

<400> SEQUENCE: 57

Gly Thr Leu Gly Ile Val Cys Pro Ile
1               5

<210> SEQ ID NO 58
<211> LENGTH: 9
<212> TYPE: PRT
<213> ORGANISM: Artificial
<220> FEATURE:
<223> OTHER INFORMATION: peptide

<400> SEQUENCE: 58

Thr Leu Gly Ile Val Cys Pro Ile Cys
1               5

<210> SEQ ID NO 59
<211> LENGTH: 12
<212> TYPE: PRT
<213> ORGANISM: Artificial
<220> FEATURE:
<223> OTHER INFORMATION: peptide

<400> SEQUENCE: 59

Met His Gly Asp Thr Pro Thr Leu His Glu Tyr Asp
1               5                   10

<210> SEQ ID NO 60
<211> LENGTH: 15
<212> TYPE: PRT
<213> ORGANISM: Artificial
<220> FEATURE:
<223> OTHER INFORMATION: peptide

<400> SEQUENCE: 60

Asp Arg Ala His Tyr Asn Ile Val Thr Phe Cys Cys Lys Cys Asp
1               5                   10                  15

<210> SEQ ID NO 61
<211> LENGTH: 14
<212> TYPE: PRT
<213> ORGANISM: Artificial
<220> FEATURE:
<223> OTHER INFORMATION: peptide

<400> SEQUENCE: 61

Asp Ser Thr Leu Arg Leu Cys Val Gln Ser Thr His Val Asp
1               5                   10

<210> SEQ ID NO 62
<211> LENGTH: 9
<212> TYPE: PRT
<213> ORGANISM: Artificial
<220> FEATURE:
<223> OTHER INFORMATION: peptide

<400> SEQUENCE: 62

Thr Leu His Glu Tyr Met Leu Asp Leu
1               5

<210> SEQ ID NO 63
<211> LENGTH: 10
<212> TYPE: PRT
<213> ORGANISM: Artificial
<220> FEATURE:
<223> OTHER INFORMATION: peptide

<400> SEQUENCE: 63

Tyr Met Leu Asp Leu Gln Pro Glu Thr Thr
1               5                   10

```
<210> SEQ ID NO 64
<211> LENGTH: 9
<212> TYPE: PRT
<213> ORGANISM: Artificial
<220> FEATURE:
<223> OTHER INFORMATION: peptide

<400> SEQUENCE: 64

Tyr Met Leu Asp Leu Gln Pro Glu Thr
1               5

<210> SEQ ID NO 65
<211> LENGTH: 9
<212> TYPE: PRT
<213> ORGANISM: Artificial
<220> FEATURE:
<223> OTHER INFORMATION: peptide

<400> SEQUENCE: 65

Met Leu Asp Leu Gln Pro Glu Thr Thr
1               5

<210> SEQ ID NO 66
<211> LENGTH: 10
<212> TYPE: PRT
<213> ORGANISM: Artificial
<220> FEATURE:
<223> OTHER INFORMATION: peptide

<400> SEQUENCE: 66

Gln Pro Glu Thr Thr Asp Leu Tyr Cys Tyr
1               5                   10

<210> SEQ ID NO 67
<211> LENGTH: 9
<212> TYPE: PRT
<213> ORGANISM: Artificial
<220> FEATURE:
<223> OTHER INFORMATION: peptide

<400> SEQUENCE: 67

Gln Ala Glu Pro Asp Arg Ala His Tyr
1               5

<210> SEQ ID NO 68
<211> LENGTH: 10
<212> TYPE: PRT
<213> ORGANISM: Artificial
<220> FEATURE:
<223> OTHER INFORMATION: peptide

<400> SEQUENCE: 68

Glu Pro Asp Arg Ala His Tyr Asn Ile Val
1               5                   10

<210> SEQ ID NO 69
<211> LENGTH: 16
<212> TYPE: PRT
<213> ORGANISM: Artificial
<220> FEATURE:
<223> OTHER INFORMATION: peptide

<400> SEQUENCE: 69

Glu Asp Glu Ile Asp Gly Pro Ala Gly Gln Ala Glu Pro Asp Arg Ala
1               5                   10                  15

<210> SEQ ID NO 70
```

<211> LENGTH: 35
<212> TYPE: PRT
<213> ORGANISM: Artificial
<220> FEATURE:
<223> OTHER INFORMATION: peptide

<400> SEQUENCE: 70

Gly Gln Ala Glu Pro Asp Arg Ala His Tyr Asn Ile Val Thr Phe Cys
1               5                   10                  15
Cys Lys Cys Asp Ser Thr Leu Arg Leu Cys Val Gln Ser Thr His Val
            20                  25                  30
Asp Ile Arg
        35

<210> SEQ ID NO 71
<211> LENGTH: 13
<212> TYPE: PRT
<213> ORGANISM: Artificial
<220> FEATURE:
<223> OTHER INFORMATION: peptide

<400> SEQUENCE: 71

Ala His Tyr Asn Ile Val Thr Phe Cys Cys Lys Cys Asp
1               5                   10

<210> SEQ ID NO 72
<211> LENGTH: 11
<212> TYPE: PRT
<213> ORGANISM: Artificial
<220> FEATURE:
<223> OTHER INFORMATION: peptide

<400> SEQUENCE: 72

Cys Cys Lys Cys Asp Ser Thr Leu Arg Leu Cys
1               5                   10

<210> SEQ ID NO 73
<211> LENGTH: 20
<212> TYPE: PRT
<213> ORGANISM: Artificial
<220> FEATURE:
<223> OTHER INFORMATION: peptide

<400> SEQUENCE: 73

Cys Asp Ser Thr Leu Arg Leu Cys Val Gln Ser Thr His Val Asp Ile
1               5                   10                  15
Arg Thr Leu Glu
        20

<210> SEQ ID NO 74
<211> LENGTH: 9
<212> TYPE: PRT
<213> ORGANISM: Artificial
<220> FEATURE:
<223> OTHER INFORMATION: peptide

<400> SEQUENCE: 74

Lys Leu Gln Cys Val Asp Leu His Val
1               5

<210> SEQ ID NO 75
<211> LENGTH: 10
<212> TYPE: PRT
<213> ORGANISM: Artificial
<220> FEATURE:
<223> OTHER INFORMATION: peptide

```
<400> SEQUENCE: 75

Phe Leu Thr Pro Lys Lys Leu Gln Cys Val
1               5                   10

<210> SEQ ID NO 76
<211> LENGTH: 10
<212> TYPE: PRT
<213> ORGANISM: Artificial
<220> FEATURE:
<223> OTHER INFORMATION: peptide

<400> SEQUENCE: 76

Val Ile Ser Asn Asp Val Cys Ala Gln Val
1               5                   10

<210> SEQ ID NO 77
<211> LENGTH: 10
<212> TYPE: PRT
<213> ORGANISM: Artificial
<220> FEATURE:
<223> OTHER INFORMATION: peptide

<400> SEQUENCE: 77

Tyr Ile Ser Asn Asp Val Cys Ala Gln Val
1               5                   10

<210> SEQ ID NO 78
<211> LENGTH: 9
<212> TYPE: PRT
<213> ORGANISM: Artificial
<220> FEATURE:
<223> OTHER INFORMATION: peptide

<400> SEQUENCE: 78

Gln Val His Pro Gln Lys Val Thr Lys
1               5

<210> SEQ ID NO 79
<211> LENGTH: 9
<212> TYPE: PRT
<213> ORGANISM: Artificial
<220> FEATURE:
<223> OTHER INFORMATION: peptide

<400> SEQUENCE: 79

Cys Tyr Ala Ser Gly Trp Gly Ser Ile
1               5

<210> SEQ ID NO 80
<211> LENGTH: 10
<212> TYPE: PRT
<213> ORGANISM: Artificial
<220> FEATURE:
<223> OTHER INFORMATION: peptide

<400> SEQUENCE: 80

His Tyr Arg Lys Trp Ile Lys Asp Thr Ile
1               5                   10

<210> SEQ ID NO 81
<211> LENGTH: 9
<212> TYPE: PRT
<213> ORGANISM: Artificial
<220> FEATURE:
<223> OTHER INFORMATION: peptide
```

```
<400> SEQUENCE: 81

Leu Leu His Glu Thr Asp Ser Ala Val
1               5

<210> SEQ ID NO 82
<211> LENGTH: 9
<212> TYPE: PRT
<213> ORGANISM: Artificial
<220> FEATURE:
<223> OTHER INFORMATION: peptide

<400> SEQUENCE: 82

Ala Leu Phe Asp Ile Glu Ser Lys Val
1               5

<210> SEQ ID NO 83
<211> LENGTH: 9
<212> TYPE: PRT
<213> ORGANISM: Artificial
<220> FEATURE:
<223> OTHER INFORMATION: peptide

<400> SEQUENCE: 83

Val Leu Ala Gly Gly Phe Phe Leu Leu
1               5

<210> SEQ ID NO 84
<211> LENGTH: 9
<212> TYPE: PRT
<213> ORGANISM: Artificial
<220> FEATURE:
<223> OTHER INFORMATION: peptide

<400> SEQUENCE: 84

Asn Tyr Ala Arg Thr Glu Asp Phe Phe
1               5

<210> SEQ ID NO 85
<211> LENGTH: 9
<212> TYPE: PRT
<213> ORGANISM: Artificial
<220> FEATURE:
<223> OTHER INFORMATION: peptide

<400> SEQUENCE: 85

Leu Tyr Ser Asp Pro Ala Asp Tyr Phe
1               5

<210> SEQ ID NO 86
<211> LENGTH: 9
<212> TYPE: PRT
<213> ORGANISM: Artificial
<220> FEATURE:
<223> OTHER INFORMATION: peptide

<400> SEQUENCE: 86

Thr Tyr Ser Val Ser Phe Asp Ser Leu
1               5

<210> SEQ ID NO 87
<211> LENGTH: 9
<212> TYPE: PRT
<213> ORGANISM: Artificial
<220> FEATURE:
<223> OTHER INFORMATION: peptide

<400> SEQUENCE: 87
```

```
Ala Leu Asp Val Tyr Asn Gly Leu Leu
1               5
```

<210> SEQ ID NO 88
<211> LENGTH: 9
<212> TYPE: PRT
<213> ORGANISM: Artificial
<220> FEATURE:
<223> OTHER INFORMATION: peptide

<400> SEQUENCE: 88

```
Leu Tyr Cys Glu Ser Val His Asn Phe
1               5
```

<210> SEQ ID NO 89
<211> LENGTH: 15
<212> TYPE: PRT
<213> ORGANISM: Artificial
<220> FEATURE:
<223> OTHER INFORMATION: peptide

<400> SEQUENCE: 89

```
Gly Gln Asp Leu Phe Gly Ile Trp Ser Lys Val Tyr Asp Pro Leu
1               5                   10                  15
```

<210> SEQ ID NO 90
<211> LENGTH: 15
<212> TYPE: PRT
<213> ORGANISM: Artificial
<220> FEATURE:
<223> OTHER INFORMATION: peptide

<400> SEQUENCE: 90

```
Thr Glu Asp Thr Met Thr Lys Leu Arg Glu Leu Ser Glu Leu Ser
1               5                   10                  15
```

<210> SEQ ID NO 91
<211> LENGTH: 9
<212> TYPE: PRT
<213> ORGANISM: Artificial
<220> FEATURE:
<223> OTHER INFORMATION: peptide

<400> SEQUENCE: 91

```
Ala Leu Gln Pro Gly Thr Ala Leu Leu
1               5
```

<210> SEQ ID NO 92
<211> LENGTH: 9
<212> TYPE: PRT
<213> ORGANISM: Artificial
<220> FEATURE:
<223> OTHER INFORMATION: peptide

<400> SEQUENCE: 92

```
Ala Ile Leu Ala Leu Leu Pro Ala Leu
1               5
```

<210> SEQ ID NO 93
<211> LENGTH: 9
<212> TYPE: PRT
<213> ORGANISM: Artificial
<220> FEATURE:
<223> OTHER INFORMATION: peptide

<400> SEQUENCE: 93

```
Ala Leu Leu Met Ala Gly Leu Ala Leu
1               5
```

<210> SEQ ID NO 94
<211> LENGTH: 10
<212> TYPE: PRT
<213> ORGANISM: Artificial
<220> FEATURE:
<223> OTHER INFORMATION: peptide

<400> SEQUENCE: 94

```
Leu Leu Cys Tyr Ser Cys Lys Ala Gln Val
1               5                   10
```

<210> SEQ ID NO 95
<211> LENGTH: 15
<212> TYPE: PRT
<213> ORGANISM: Artificial
<220> FEATURE:
<223> OTHER INFORMATION: peptide

<400> SEQUENCE: 95

```
Leu Leu Ala Asn Gly Arg Met Pro Thr Val Leu Gln Cys Val Asn
1               5                   10                  15
```

<210> SEQ ID NO 96
<211> LENGTH: 15
<212> TYPE: PRT
<213> ORGANISM: Artificial
<220> FEATURE:
<223> OTHER INFORMATION: peptide

<400> SEQUENCE: 96

```
Arg Met Pro Thr Val Leu Gln Cys Val Asn Val Ser Val Val Ser
1               5                   10                  15
```

<210> SEQ ID NO 97
<211> LENGTH: 15
<212> TYPE: PRT
<213> ORGANISM: Artificial
<220> FEATURE:
<223> OTHER INFORMATION: peptide

<400> SEQUENCE: 97

```
Ser Val Ser Glu Ser Asp Thr Ile Arg Ser Ile Ser Ile Ala Ser
1               5                   10                  15
```

<210> SEQ ID NO 98
<211> LENGTH: 9
<212> TYPE: PRT
<213> ORGANISM: Artificial
<220> FEATURE:
<223> OTHER INFORMATION: peptide

<400> SEQUENCE: 98

```
Phe Leu Arg Gly Arg Ala Tyr Gly Leu
1               5
```

<210> SEQ ID NO 99
<211> LENGTH: 9
<212> TYPE: PRT
<213> ORGANISM: Artificial
<220> FEATURE:
<223> OTHER INFORMATION: peptide

<400> SEQUENCE: 99

```
Phe Leu Phe Leu Leu Phe Phe Trp Leu
```

-continued

```
1               5

<210> SEQ ID NO 100
<211> LENGTH: 9
<212> TYPE: PRT
<213> ORGANISM: Artificial
<220> FEATURE:
<223> OTHER INFORMATION: peptide

<400> SEQUENCE: 100

Thr Leu Met Ser Ala Met Thr Asn Leu
1               5

<210> SEQ ID NO 101
<211> LENGTH: 9
<212> TYPE: PRT
<213> ORGANISM: Artificial
<220> FEATURE:
<223> OTHER INFORMATION: peptide

<400> SEQUENCE: 101

Ala Leu Asp Val Tyr Asn Gly Leu Leu
1               5

<210> SEQ ID NO 102
<211> LENGTH: 9
<212> TYPE: PRT
<213> ORGANISM: Artificial
<220> FEATURE:
<223> OTHER INFORMATION: peptide

<400> SEQUENCE: 102

Ile Leu Leu Trp Gln Pro Ile Pro Val
1               5

<210> SEQ ID NO 103
<211> LENGTH: 9
<212> TYPE: PRT
<213> ORGANISM: Artificial
<220> FEATURE:
<223> OTHER INFORMATION: peptide

<400> SEQUENCE: 103

Leu Leu Leu Gly Thr Ile His Ala Leu
1               5

<210> SEQ ID NO 104
<211> LENGTH: 33
<212> TYPE: PRT
<213> ORGANISM: Artificial
<220> FEATURE:
<223> OTHER INFORMATION: peptide

<400> SEQUENCE: 104

Cys His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala

<210> SEQ ID NO 105
<211> LENGTH: 501
<212> TYPE: PRT
<213> ORGANISM: Artificial
<220> FEATURE:
<223> OTHER INFORMATION: peptide
```

<400> SEQUENCE: 105

Met Ala Val Met Ala Pro Arg Thr Leu Val Leu Leu Leu Ser Gly Ala
1               5                   10                  15

Leu Ala Leu Thr Gln Thr Trp Ala Phe Leu Trp Gly Pro Arg Ala Leu
            20                  25                  30

Val Gly Gly Gly Ser Gly Gly Gly Ser Gly Gly Gly Gly Ser
            35                  40                  45

Gly Gly Gly Ser Gly Ile Gln Arg Thr Pro Lys Ile Gln Val Tyr Ser
50                  55                  60

Arg His Pro Ala Glu Asn Gly Lys Ser Asn Phe Leu Asn Cys Tyr Val
65                  70                  75                  80

Ser Gly Phe His Pro Ser Asp Ile Glu Val Asp Leu Leu Lys Asn Gly
                85                  90                  95

Glu Arg Ile Glu Lys Val Glu His Ser Asp Leu Ser Phe Ser Lys Asp
            100                 105                 110

Trp Ser Phe Tyr Leu Leu Tyr Tyr Thr Glu Phe Thr Pro Thr Glu Lys
            115                 120                 125

Asp Glu Tyr Ala Cys Arg Val Asn His Val Thr Leu Ser Gln Pro Lys
130                 135                 140

Ile Val Lys Trp Asp Arg Asp Met Gly Gly Gly Ser Gly Gly Gly
145                 150                 155                 160

Gly Ser Gly Gly Gly Ser Gly Ser His Ser Met Arg Tyr Phe Phe
                165                 170                 175

Thr Ser Val Ser Arg Pro Gly Arg Gly Glu Pro Arg Phe Ile Ala Val
            180                 185                 190

Gly Tyr Val Asp Asp Thr Gln Phe Val Arg Phe Asp Ser Asp Ala Ala
        195                 200                 205

Ser Gln Arg Met Glu Pro Arg Ala Pro Trp Ile Glu Gln Glu Gly Pro
210                 215                 220

Glu Tyr Trp Asp Gly Glu Thr Arg Lys Val Lys Ala His Ser Gln Thr
225                 230                 235                 240

His Arg Val Asp Leu Gly Thr Leu Arg Gly Tyr Tyr Asn Gln Ser Glu
                245                 250                 255

Ser His Thr Val Gln Arg Met Tyr Gly Cys Asp Val Gly Ser Asp Trp
            260                 265                 270

Arg Phe Leu Arg Gly Tyr His Gln Tyr Ala Tyr Asp Gly Lys Asp Tyr
            275                 280                 285

Ile Ala Leu Lys Glu Asp Leu Arg Ser Trp Thr Ala Ala Asp Met Ala
        290                 295                 300

Ala Gln Thr Thr Lys His Lys Trp Glu Ala Ala His Val Ala Glu Gln
305                 310                 315                 320

Leu Arg Ala Tyr Leu Glu Gly Thr Cys Val Glu Trp Leu Arg Arg Tyr
                325                 330                 335

Leu Glu Asn Gly Lys Glu Thr Leu Gln Arg Thr Asp Ser Pro Lys Ala
            340                 345                 350

His Val Thr His His Pro Arg Ser Lys Gly Glu Val Thr Leu Arg Cys
        355                 360                 365

Trp Ala Leu Gly Phe Tyr Pro Ala Asp Ile Thr Leu Thr Trp Gln Leu
            370                 375                 380

Asn Gly Glu Glu Leu Thr Gln Asp Met Glu Leu Val Glu Thr Arg Pro
385                 390                 395                 400

Ala Gly Asp Gly Thr Phe Gln Lys Trp Ala Ser Val Val Val Pro Leu

```
                    405                 410                 415
Gly Lys Glu Gln Asn Tyr Thr Cys Arg Val Tyr His Glu Gly Leu Pro
            420                 425                 430

Glu Pro Leu Thr Leu Arg Trp Glu Pro Pro Ser Thr Asp Ser Tyr
        435                 440                 445

Met Val Ile Val Ala Val Leu Gly Val Leu Gly Ala Met Ala Ile Ile
    450                 455                 460

Gly Ala Val Val Ala Phe Val Met Lys Arg Arg Asn Thr Gly Gly
465                 470                 475                 480

Gly Asp Tyr Ala Leu Ala Pro Gly Ser Gln Ser Ser Glu Met Ser Leu
                485                 490                 495

Arg Asp Cys Lys Ala
            500

<210> SEQ ID NO 106
<211> LENGTH: 5
<212> TYPE: PRT
<213> ORGANISM: Artificial
<220> FEATURE:
<223> OTHER INFORMATION: peptide
<220> FEATURE:
<221> NAME/KEY: REPEAT
<222> LOCATION: (1)..(5)
<223> OTHER INFORMATION: Linker consisting of (GGGGS)n

<400> SEQUENCE: 106

Gly Gly Gly Gly Ser
1               5

<210> SEQ ID NO 107
<211> LENGTH: 6
<212> TYPE: PRT
<213> ORGANISM: Artificial
<220> FEATURE:
<223> OTHER INFORMATION: peptide
<220> FEATURE:
<221> NAME/KEY: REPEAT
<222> LOCATION: (1)..(6)
<223> OTHER INFORMATION: Linker consiting of (GSTSGS)n

<400> SEQUENCE: 107

Gly Ser Thr Ser Gly Ser
1               5

<210> SEQ ID NO 108
<211> LENGTH: 18
<212> TYPE: PRT
<213> ORGANISM: Artificial
<220> FEATURE:
<223> OTHER INFORMATION: peptide

<400> SEQUENCE: 108

Gly Ser Thr Ser Gly Ser Gly Lys Pro Gly Ser Gly Glu Gly Ser Thr
1               5                   10                  15

Lys Gly

<210> SEQ ID NO 109
<211> LENGTH: 23
<212> TYPE: PRT
<213> ORGANISM: Artificial
<220> FEATURE:
<223> OTHER INFORMATION: peptide

<400> SEQUENCE: 109
```

-continued

```
Gly Phe Ala Lys Thr Thr Ala Pro Ser Val Tyr Pro Leu Ala Pro Val
1               5                   10                  15

Leu Glu Ser Ser Gly Ser Gly
            20

<210> SEQ ID NO 110
<211> LENGTH: 10
<212> TYPE: PRT
<213> ORGANISM: Artificial
<220> FEATURE:
<223> OTHER INFORMATION: peptide

<400> SEQUENCE: 110

Glu Pro Lys Ser Cys Asp Lys Thr His Thr
1               5                   10

<210> SEQ ID NO 111
<211> LENGTH: 12
<212> TYPE: PRT
<213> ORGANISM: Artificial
<220> FEATURE:
<223> OTHER INFORMATION: peptide

<400> SEQUENCE: 111

Glu Leu Lys Thr Pro Leu Gly Asp Thr Thr His Thr
1               5                   10

<210> SEQ ID NO 112
<211> LENGTH: 7
<212> TYPE: PRT
<213> ORGANISM: Artificial
<220> FEATURE:
<223> OTHER INFORMATION: peptide

<400> SEQUENCE: 112

Glu Ser Lys Tyr Gly Pro Pro
1               5
```